(12) United States Patent
Huchel et al.

(10) Patent No.: US 8,466,294 B2
(45) Date of Patent: Jun. 18, 2013

(54) 1-AZA-3,7-DIOXABICYCLO[3.3.0]OCTANE COMPOUNDS AND THEIR USE AS PRO-FRAGRANCES

(75) Inventors: Ursula Huchel, Cologne (DE); Silvia Sauf, Dusseldorf (DE); Thomas Gerke, Neuss (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 80 days.

(21) Appl. No.: 12/175,221

(22) Filed: Jul. 17, 2008

(65) Prior Publication Data

US 2008/0305063 A1 Dec. 11, 2008

Related U.S. Application Data

(63) Continuation of application No. PCT/EP2007/000238, filed on Jan. 12, 2007.

(30) Foreign Application Priority Data

Jan. 20, 2006 (DE) .......................... 10 2006 003 092

(51) Int. Cl.
*C07D 498/04* (2006.01)
*A61K 31/424* (2006.01)
*A61K 8/49* (2006.01)

(52) U.S. Cl.
USPC .......... 548/218; 514/375; 424/401; 424/70.1; 424/65

(58) Field of Classification Search
USPC .................. 548/218; 514/375; 424/401, 70.1, 424/65
See application file for complete search history.

(56) References Cited

U.S. PATENT DOCUMENTS

| | | | |
|---|---|---|---|
| 4,277,353 A | | 7/1981 | Deen et al. |
| 4,277,354 A | * | 7/1981 | Brois et al. ..................... 508/270 |
| 6,861,402 B1 | | 3/2005 | Miracle et al. |
| 2003/0158079 A1 | | 8/2003 | Dykstr |
| 2003/0207786 A1 | | 11/2003 | Miracle |
| 2004/0116647 A1 | * | 6/2004 | Swedo .......................... 528/145 |
| 2005/0054787 A1 | * | 3/2005 | Swedo et al. ................. 525/534 |

FOREIGN PATENT DOCUMENTS

| | | | |
|---|---|---|---|
| CN | 1603315 A | * | 4/2005 |
| CN | 1785995 A | * | 6/2006 |
| DE | 1133847 | | 7/1962 |
| WO | WO2004/009564 | | 1/2004 |

OTHER PUBLICATIONS

Crabb et al. Tetrahedron 1973, 29(21), 3389-98.*
Zayed et al. Pakistan Journal of Scientific & Industrial Research 1987, 30(6), 432-38.*
Maiereanu et al. Heterocyclic Communications 2005, 11(3-4), 305-310.*
Maslinska-Solich et al. Polimery (Warsaw, Poland) 2005, 50(7/8), 509-519.*
Abstract for CN 1785995 A (Jun. 14, 2006).*
R. Nouguier m Crozet Reactivitè du Tris(Hydroxymethyl)aminomethane avec des Niro-Aldehydes Aromatiques. Synthese de Nouveaux Composès Antimicrobiens "Tetrahedron Letters" Bd. 2, N. 4 (1985), pp. 5523-5524.
J.S. Pierce et al., "Tris-(hydroxymethyl)-aminomethane Devrivaties ((( Oxamides., Ureas Oxazolidines and 1-Aza-3,7-dioxabicyclo(3.30)octanes" Hournal of the American Chemical Society, (1951), pp. 2595-2596.
M. Senkus "Some New Derivatives of Amino Hydroxy Compounds" Journal of the American Chemical Society (1945), pp. 1515-1519.

* cited by examiner

*Primary Examiner* — Jason M Nolan
(74) *Attorney, Agent, or Firm* — David LeCroy

(57) ABSTRACT

1-aza-3,7-dioxabicyclo[3.3.0]octane compounds, process for their preparation, their use as pro-fragrances, and washing and cleaning compositions, fabric softeners and cosmetics comprising them, and a process for prolonging the odor perception of such compositions.

14 Claims, No Drawings

1-AZA-3,7-DIOXABICYCLO[3.3.0]OCTANE COMPOUNDS AND THEIR USE AS PRO-FRAGRANCES

CROSS-REFERENCE TO RELATED APPLICATIONS

This application is a continuation under 35 U.S.C. Section 365(c) and 35 U.S.C. Section 120 of International Application No. PCT/EP2007/000238, filed Jan. 12, 2007. This application also claims priority under 35 U.S.C. Section 119 of German Patent Application No. DE 10 2006 003 092.3, filed Jan. 20, 2006. Both the International Application and the German Application are incorporated herein by reference in their entireties.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION (1) Field of the Invention

The invention relates to 1-aza-3,7-dioxabicyclo[3.3.0]octane compounds, methods for their preparation, their use as pro-fragrances and detergents and cleaning agents containing same, fabric softeners and cosmetics as well as a method for prolonging the scent perception of such agents.

In addition to the direct addition of scent substances to detergents and cleaning agents, fabric softeners and cosmetics, the addition of pro-fragrances has also been proposed. By analogy with pro-drugs, pro-fragrances are chemical derivatives of a scent, which reduce the volatility of the scent, for example, and allows a delayed release of the scent over time under ambient conditions. By derivatization of scents, such as scent aldehydes or scent ketones, the vapor pressure of these compounds can be lowered. Since the derivatization reaction is reversible, the chemically bound perfume aldehyde or perfume ketone may, under certain conditions, e.g., ambient conditions, be cleaved at the bonding site. This releases the perfume or scent substance again, which may lead to a prolonged scent impression.

(2) Description of Related Art, Including Information Disclosed Under 37 C.F.R. Sections 1.97 and 1.98

DE-A-1 333 847 relates to the use of the condensation products of aldehydes and ketones with oxyamines in perfumery. To do so, the aldehydes and ketones are reacted with ethanolamine or diethanolamine.

U.S. Pat. No. 6,861,402 describes pro-fragrances containing a scent aldehyde or a scent ketone bound in the form of an oxazolidine. For example, N-benzene-ethanolamine is reacted with a scent to yield a monocyclic oxazolidine.

US-A-2003/0207786 also describes pro-fragrances having an oxazolidine structure.

WO 2004/009564 A2 relates to cyclic co-surfactants, which are formed by a condensation reaction of $C_3$-$C_6$ aldehydes with polyvalent alcohols, amines, thiols or carboxylic acids. The co-surfactants are suitable for use in household detergents, household cleaning products, body cleaning agents and body care agents.

BRIEF SUMMARY OF THE INVENTION

The object of the present invention is now to provide alternative scent precursors, pro-fragrances.

The object of the present invention is also to provide pro-fragrances which allow a prolonged scent impression with scent aldehydes and scent ketones, which have a high vapor pressure per se.

In particular, the object was to provide hydrolysis-stable pro-fragrances which could also be incorporated into aqueous detergents and cleaning agents without being subject to excessive hydrolysis phenomenon even in the product. The ability to incorporate the compounds in granular detergent and cleaning agent compositions without resulting in decomposition during the production process is a requirement of the compounds to be made available. In addition, the substrates treated with the inventive compounds should have a pleasant and long-lasting scent.

It has surprisingly now been found that very good pro-fragrances are obtained for scents that are present in derivatized form as 1-aza-3,7-dioxabicyclo[3.3.0]octane compounds (bicyclic oxazolidine derivatives). These compounds are easily obtained for use in detergents and cleaning agents as well as in cosmetic preparations.

This object is therefore achieved according to this invention by 1-aza-3,7-dioxabicyclo[3.3.0]octane compounds of general formula (I)

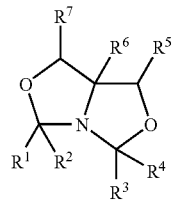

wherein
$R^1$, $R^2$,
$R^3$, $R^4$ independently of one another denote radicals that yield a scent aldehyde or a scent ketone in a compound of general formula $R^1$—C(=O)—$R^2$ and/or $R^3$—C(=O)—$R^4$, wherein $R^1$ and $R^2$ and/or $R^3$ and $R^4$ may not be hydrogen at the same time,
$R^6$ denotes H, alkyl, which may be substituted by one or two hydroxyl groups and/or an amino group and/or in which up to eight nonvicinal $CH_2$ groups may be replaced by O,
$R^5$, $R^7$ independently of one another denote H or $C_1$ to $C_6$ alkyl
or mixtures of these compounds.

This object is also achieved by mixtures of the compounds of general formula (I) and compounds of general formula (II)

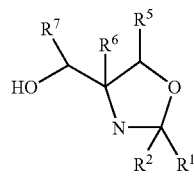

having the meanings given above for $R^1$, $R^2$, $R^5$, $R^6$ and $R^7$.

The inventive compounds of general formula (I) and/or the mixtures containing these compounds are used according to this invention as prodrug fragrances, in particular in detergents and cleaning agents, fabric softeners and cosmetics.

The present invention thus relates to detergents or cleaning agents, fabric softeners or cosmetics, which have compounds of general formula (I) or mixtures containing them.

The invention also relates to a method for prolonging the scent perception of detergents and cleaning agents, fabric softeners and cosmetics or solid surfaces treated with these, whereby compounds of general formula (I) or mixtures containing same are incorporated into the cleaning agents or detergents, fabric softeners or cosmetics.

BRIEF DESCRIPTION OF THE SEVERAL VIEWS OF THE DRAWING(S)

Not Applicable

DETAILED DESCRIPTION OF THE INVENTION

Oil-soluble substituted monocyclic and bicyclic oxazolidines which are used as additives in automatic transmission fluids, for example, are known from U.S. Pat. No. 4,277,353. Examples described include reaction products of optionally substituted 2-amino-1,3-propanediols with paraformaldehyde and isobutyraldehyde. Derivatization of scent aldehydes or scent ketones, however, is not mentioned. According to one embodiment of the present invention, the following compounds are excluded: 1-aza-3,7-dioxa-5-methylbicyclo[3.3.0]octane, 1-aza-3,7-dioxa-5-ethylbicyclo[3.3.0]octane, 1-aza-3,7-dioxabicyclo[3.3.0]octane and 1-aza-3,7-dioxa-2,8-diisopropyl-5-ethylbicyclo[3.3.0]octane. Furthermore, according to one embodiment of the present invention, $R^1$ and $R^3$ are not $C_1$-$C_{30}$ hydrocarbyl radicals if $R^2$ and $R^4$ and $R^5$ and $R^7$ are hydrogen and $R^6$ is hydrogen, methyl or ethyl. Furthermore, according to one embodiment of the invention, compounds in which the radical $R^1$ is a $C_1$-$C_{30}$ hydrocarbyl radical and $R^2$ is hydrogen and in the structural element —$CR^3R^4$ the radicals $R^3$ and $R^4$ each denote $C_1$-$C_7$ hydrocarbyl radicals are excluded.

It has been found according to this invention that bicyclic oxazolidine derivatives of scent aldehydes and scent ketones allow a reduction in vapor pressure of the scent aldehydes and scent ketones and prolong the scent impression. Furthermore, the deposition of the bicyclic compounds on solid surfaces such as textiles, skin or hard surfaces can be improved.

The inventive compounds of general formula (I) are obtained by reacting compounds of general formula (III)

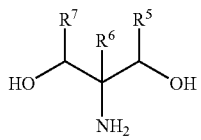

with compounds of general formula $R^1$—C(=O)—$R^2$ and $R^3$—C(=O)—$R^4$ with ring closure.

The compounds of general formula (III) are derived from 2-amino-1,3-propanediol. By producing the bicyclic compounds, it is possible to achieve a high degree of loading of the 2-amino-1,3-propanediols, so that the use of smaller amounts of 2-amino-1,3-propanediols is necessary. This achieves a lengthening of the scent impression even with smaller amounts of 2-amino-1,3-propanediols, which can lead to cost advantages and also avoids the introduction of large quantities of chemicals into detergents or cleaning agents, fabric softeners, or cosmetics.

It is also possible according to this invention to use compounds based on 2-amino-1,3-propanediols with one or two ring closures. It is preferable to achieve a high degree of loading of the 2-amino-1,3-propanediols, so that 2-amino-1,3-propanediols that are reacted twice are preferably used.

In the compounds of general formula (I), $R^1$, $R^2$, $R^3$ and $R^4$, independently of one another, denote radicals that yield a scent aldehyde or a scent ketone in a compound of the general formula $R^1$—C(=O)—$R^2$ and/or $R^3$—C(=O)—$R^4$. $R^1$ and $R^2$ and/or $R^3$ and $R^4$ need not be hydrogen at the same time. The radicals $R^1$ and $R^2$ in the structural element —$CR^1R^2$ and the radicals $R^3$ and $R^4$ in the structural element —$CR^3R^4$ together preferably have at least six carbon atoms, preferably at least five carbon atoms, especially preferably at least four carbon atoms.

According to this invention, one of the structural elements —$CR^1R^2$ and/or —$CR^3R^4$ has radicals $R^1$ and $R^2$ and/or $R^3$ and $R^4$ which yield a scent ketone in a compound of general formula $R^1$—C(=O)—$R^2$ and $R^3$—C(=O)—$R^4$.

In a preferred embodiment, $R^2$, $R^4$, $R^5$, $R^6$, $R^7$ denote hydrogen and $R^1$ and $R^3$ each denote a $C_{4-24}$ hydrocarbon radical.

In the compounds of general formula (I), scent aldehydes and/or scent ketones which are reacted with 2-amino-1,3-propanediols of general formula (II) are thus present. All the conventional scent aldehydes and scent ketones which are typically used to achieve a pleasant scent perception may be used as the scent aldehydes or scent ketones. Those skilled in the art are aware of suitable scent aldehydes and scent ketones, which are described in US-A-2003/0158079 Paragraphs [0154] and [0155] and in U.S. Pat. No. 6,861,402, the entire contents of each of which are incorporated herein by reference.

Scent ketones may include all ketones that can impart a desired scent or a fresh perception. Mixtures of different ketones may also be used. For example, the ketone may be selected from the group comprising buchu oxime; isojasmone; methyl-β-naphthyl ketone, musk indanone; tonalide/musk plus; α-damascone, β-damascone, δ-damascone, isodamascone, damascenone, damarose, methyl dihydrojasmonate, menthone, carvone, camphor, fenchone, α-ionene, β-ionone, dihydro-β-ionone, γ-methyl, ionone, fleuramone, dihydrojasmone, cis-jasmone, iso-E-super, methyl cedrenyl ketone or methyl cedrylone, acetophenone, methyl acetophenone, paramethoxyacetophenone, methyl-β-naphthyl ketone, benzylacetone, benzophenone, parahydroxy-phenylbutanone, celery ketone or livescone, 6-isopropyl-decahydro-2-naphthone, dimethyloctenone, freskomenth, 4-(1-ethoxyvinyl)-3,3,5,5-tetramethylcyclohexanone, methylheptenone, 2-(2-(4-methyl-3-cyclohexen-1-yl)propyl)cyclopentanone, 1-(p-menthen-6(2)-yl)-1-propanone, 4-(4-hydroxy-3-methoxyphenyl)-2-butanone, 2-acetyl-3,3-dimethylnorbornane, 6,7-dihydro-1,1,2,3,3-pentamethyl-4(5H)indanone, 4-damascole, dulcinyl or cassion, gelsone, hexylone isocyclemon E, methyl cyclocitron, methyl lavendel ketone, orivone, para-tert-butylcyclohexanone, verdone, delphone, muscone, neobutenone, plicatone, veloutone, 2,4,4,7-tetramethyloct-6-en-3-one, tetramerane, hedione and mixtures thereof. The ketones may preferably be selected from α-damascone, δ-damascone isodamascone, carvone, γ-methylionone, iso-E-super, 2,4,4,7-tetramethyloct-6-en-3-one, benzylacetone, β-damascone, damascenone, methyl dihydrojasmonate, methyl cedrylone, hedione and mixtures thereof.

Suitable scent aldehydes may be any aldehydes which impart a desired scent or a fresh perception according to the scent ketones. These may again be individual aldehydes or aldehyde mixtures. Suitable aldehydes include, for example, melonal, triplal, ligustral, adoxal; anisaldehyde; cymal; ethyl vanillin; florhydral; helional; heliotropin; hydroxycitronellal; koavone; lauryl aldehyde, lyral, methyl nonylacetaldehyde; p,t-bucinal; phenyl acetaldehyde; undecylene aldehyde; vanillin; 2,6,10-trimethyl-9-undecenal, 3-dodecen-l-al, α-n-amylcinnamaldehyde, 4-methoxybenzaldhyde, benzaldehyde, 3-(4-tert-butylphenyl)propanal, 2-methyl-3-(para-methoxyphenylpropanal), 2-methyl-4-(2,6,6-trimethyl-2(1)-cyclohexen-1-yl)butanal, 3-phenyl-2-propenal, cis-/trans-3,7-dimethyl-2,6-octadien-1-al, 3,7-dimethyl-6-octen-l-al, [(3,7-dimethyl-6-octenyl)oxy]acetaldehyde, 4-isopropylbenzaldehyde, 1,2,3,4,5,6,7,8-octahydro-8,8-dimethyl-2-naphthaldehyde, 2,4-dimethyl-3-cyclo-hexen-1-carboxyaldehyde, 2-methyl-3(isopropylphenyl)propanal, decylaldehyde, 2,6-dimethyl-5-heptenal; 4-(tricyclo[5.2.1.0 (2,6)]decylidene-8)butanal; octahydro-4,7-methano-1H-indenecarboxaldehyde; 3-ethoxy-4-hydroxybenzaldehyde, para-ethyl-α,α-dimethylhydrocinnamaldehyde, α-methyl-3, 4(methylenedioxy)hydrocinnamaldehyde, 3,4-methylenedioxybenzaldehyde, α-n-hexylcinnamaldehyde, m-cymene-7-carboxaldehyde, α-methylphenylacetaldehyde, 7-hydroxy-3,7-dimethyloctanal, undecenal, 2,4,6-trimethyl-3-cyclohexene-1-carboxaldehyde, 4-(3)(4-methyl-3-pentenyl)-3cyclohexene carboxaldehyde, 1-dodecanal, 2,4-dimethylcyclohexene-3-carboxaldehyde, 4-(4-hydroxy-4-methylpentyl)-3-cyclohexene-1-carboxaldehyde, 7-methoxy-3,7-dimethyloctan-1-al, 2-methylundecanal, 2-methyldecanal, 1-nonanal, 1-octanal, 2,6,10-trimethyl-5,9-undecadienal, 2-methyl-3-(4-tert-1-butyl)propanal, dihydrocinnamaldehyde, 1-methyl-4-(4-methyl-3-pentenyl)-3-cyclohexene-1-carboxaldehyde, 5- or 6-methoxyhexahydro-4,7-methanoindan-1- or 2-carboxyaldehyde; 3,7-dimethyloctan-1-al, 1-undecanal, 10-undecen-1-al, 4-hydroxy-3-methoxybenzaldehyde, 1-methyl-3-(4-methyl pentyl)-3-cyclohexenecarboxyaldehyde, 7-hydroxy-3,7-dimethyloctanal; trans-4-decenal, 2,6-nonadienal, para-tolylacetaldehyde; 4-methylphenylacetaldehyde, 2-methyl-4-(2, 6,6-trimethyl-1-cyclohexen-yl)-2-butenal, ortho-methoxycinnamaldehyde, 3,5,6-trimethyl-3-cyclohexenecarboxaldehyde; 3,7-dimethyl-2-methylene-6-octenal, phenoxyacetaldehyde; 5,9-dimethyl-4,8-decadienal, peony aldehyde (6,10-dimethyl-3-oxa-5,9-undecadien-1-al), hexahydro-4,7-methanoindane-1-carboxaldehyde, 2-methyloctanal, α-methyl-4-(1-methylethyl)-benzeneacetaldehyde, 6,6-dimethyl-2-norpinene-2-propionaldehyde, para-methylphenoxy-acetaldehyde; 2-methyl-3-phenyl-2-propen-1-al, 3,5,5-trimethylhexanal, hexahydro-8,8-dimethyl-2-naphthaldehyde, 3-propylbicyclo[2.2.1]-hept-5-ene-2-carbaldehyde, 9-decenal, 3-methyl-5-phenyl-1-pentanal, methylnonylacetaldehyde, 1-p-menthene-q-carboxaldehyde, citral or mixtures thereof, lilial citral, 1-decanal, florhydral, 2,4-dimethyl-3-cyclohexene-1-carboxaldehyde; preferred aldehydes may be selected from cis/trans-3,7-dimethyl-2,6octadien-l-al; heliotropin; 2,4,6-trimethyl-3-cyclohexene-1-carboxaldehyde; 2,6-nonadienal; α-n-amyl-cinnamaldehyde, α-n-hexylcinnamaldehyde, p-tert-bucinal; lyral, cymal, methyl-nonylacetaldehyde, trans-2-nonenal, lilial, trans-2-nonenal and mixtures thereof.

For additional suitable scent substances selected from aldehydes and ketones, reference is made to Steffen Arctander, published 1960 and 1969, respectively, reprinted 2000 ISBN: Aroma Chemicals, vol. 1: 0-931710-37-5, Aroma Chemicals, vol. 2: 0-931710-38-3.

As already explained above, for example, the scent aldehydes and scent ketones may have an aliphatic, cycloaliphatic, aromatic, ethylenically unsaturated structure of a combination of these structures. Furthermore, additional heteroatoms or polycyclic structures may also be present. The structures may have suitable substituents such as hydroxyl groups or amino groups.

In the most general form, a 2-amino-1,3-propanediol may be reacted with aldehydes, ketones or mixtures of ketones and aldehydes to produce the compounds of general formula (I). According to one embodiment of the invention, the compounds of general formula (I) are derived from a 2-amino-1, 3-propanediol molecule and two aldehyde molecules or one aldehyde molecule and one ketone molecule. In the reaction of less than stoichiometric amounts of aldehydes and/or ketones, monocyclic compounds are also present in the product mixture. The amount of bicyclic compounds to monocyclic compounds may be adjusted easily through the choice of the molar ratios between aldehyde/ketone and 2-amino-1,3-propanediol. Large amounts of bicyclic structures are especially preferred. Such mixtures preferably contain at least 50 wt %, preferably at least 65 wt %, in particular at least 80 wt % of bicyclic structures.

The inventive compounds of general formula (I) are produced starting from 2-amino-1,3-propanediols of general formula (III), wherein $R^3$ may denote hydrogen or alkyl, which may be substituted by one or two hydroxyl groups and/or one amino group, and up to eight nonvicinal —$CH_2$ groups may also be replaced by —O—. Alkyl radicals are preferably $C_{1-24}$ alkyl radicals, especially preferably $C_{1-16}$ alkyl radicals, in particular $C_{1-12}$ alkyl radicals, specifically $C_{1-6}$ alkyl radicals, e.g., $C_{1-3}$ alkyl radicals. Alkyl radicals may be linear, branched or cyclic. These are preferably linear alkyl radicals. They may also be mono- or dihydroxyalkyl radicals, which may also have one amino group instead of or in addition to the hydroxyl groups. The alkyl radicals may also be substituted or unsubstituted. If the alkyl radicals are interrupted by —O—, they are preferably structural elements of the formula —$CH_2$—$CH_2$—O— or —$CH_2$—$CH(CH_3)$—O—. Such compounds are easily accessible by alkoxylation of the corresponding hydroxyl compounds.

Especially preferred $R^6$ radicals include methyl-, ethyl- and hydroxymethyl radicals.

$R^5$ and $R^7$ are hydrogen or a $C_1$ to $C_6$ alkyl radical, preferably $C_1$ to $C_3$ alkyl radical. $R^5$ and $R^7$ are especially preferably hydrogen or a methyl or ethyl radical, in particular hydrogen.

The inventive compounds of general formula (I) are produced by reacting the compounds of general formula (III) with compounds of general formulas $R^1$—C(=O)—$R^2$ and $R^3$—C(=O)—$R^4$ with ring closure. The reaction is preferably performed in a suitable solvent or in situ. Suitable solvents include, for example, hydrocarbons containing aromatics, e.g., toluene. The reaction is preferably performed at a temperature in the range of 80 to 150° C., especially preferably 100 to 140° C. For example, the compound of general formula (III) is used as the starting material under a nitrogen atmosphere together with the desired ketone or aldehyde in the solvent. Then the reaction mixture is heated, whereupon the solids gradually go into solution. The mixture is then often heated at reflux on a water separator. The resulting reaction product is isolated by conventional methods and purified if necessary.

The inventive compounds of general formula (I) or the mixture containing them are used according to the invention as pro-fragrances. The term "pro-fragrance" describes derivatives of scent aldehydes and scent ketones which release the original scent aldehydes and scent ketones under ambient conditions. Ambient conditions are the typical ambient conditions in the human biosphere and/or the conditions encountered on human skin. The compounds of general formula (I) disintegrate slowly under ambient conditions in a reversal of the synthesis process, releasing the original scent aldehydes and/or scent ketones. The chemically bound perfume aldehydes and perfume ketones are cleaved at the binding site, thereby releasing the perfume substances again.

Accordingly, the use of the inventive compound as pro-fragrances, which as scent substances preferably release scent aldehydes or scent ketones, is especially preferred.

The inventive pro-fragrances may be used as the single scent substance, but it is also possible to use mixtures of scent substances, which are comprised only partially of the inventive pro-fragrances. In particular, scent substance mixtures containing 1 to 50 wt %, preferably 5 to 40 wt % and in particular max. 30 wt % of inventive pro-fragrances may be used. In other embodiments in which the delayed scent effect of the carrier-bound form is to be used, in particular, advantageously at least 30 wt %, preferably at least 40 wt % and, in particular, at least 50 wt % of the total perfume contained in an agent is introduced into the agent via the inventive pro-fragrances with the inventive use, whereas the remaining 70 wt %, preferably 60 wt % and, in particular, 50 wt % of the total perfume present in the agent is sprayed as usual or is otherwise introduced into the agent. The inventive use may thus advantageously be wherein the inventive pro-fragrances are used together with other scent substances.

Through the distribution of the total perfume content of an agent, e.g., a detergent or cleaning agent in perfume, which is present in the form of the inventive pro-fragrances and perfume that has been incorporated traditionally, a variety of product characteristics can be implemented which become possible only through the inventive use. For example, it is conceivable and possible to divide the total perfume content of an agent into two portions, x and y, whereby the portion x comprises inventive pro-fragrances and the portion y comprises traditional perfume oils.

The only limit with the inventive pro-fragrances is that the scents which are introduced via the inventive pro-fragrances must originate from the group of scent aldehydes or scent ketones.

The scent substances that may be incorporated into the agents in the traditional way are, however, not subject to any restrictions. Individual perfume substance compounds of natural or synthetic origin, e.g., of the type of esters, ethers, aldehydes, ketones, alcohols and hydrocarbons may thus be used as the perfume oils and/or scent substances. Perfume substance compounds of the ester type include, for example, benzyl acetate, phenoxyethyl isobutyrate, p-tert-butylcyclohexyl acetate, linalyl acetate, dimethylbenzylcarbinyl acetate (DMBCA), phenylethyl acetate, benzyl acetate, ethylmethyl phenyl glycinate, allylcyclohexyl propionate, styrallyl propionate, benzyl salicylate, cyclohexylsalicylate, floramat, melusat and jasmacyclate. The ethers include, for example, benzylethyl ether and ambroxan; the aldehydes include, for example, the linear alkanals with 8 to 18 carbon atoms, citral, citronellal, citronellyl oxyacetaldehyde, cyclamenaldehyde, lilial and bourgeonal; the ketones include, for example, the ionones, α-isomethylionone and methyl cedryl ketone; the alcohols include anethole, citronellol, eugenol, geraniol, linalool, phenylethyl alcohol and terpineol; the hydrocarbons include mainly terpenes such as limonene and pinene. However, mixtures of various perfume substances which jointly produce an attractive scent note are preferred.

Such perfume oils may also contain mixtures of natural perfume substances such as those accessible from plant sources, e.g., pine oil, citrus oil, jasmine oil, patchouli oil, rose oil or ylang-ylang oil. Also suitable are muscatel sage oil, chamomile oil, clove oil, lemon balm oil, mint oil, cinnamon leaf oil, linden blossom oil, juniper berry oil, vetiver oil, olibanum oil, galbanum oil and labdanum oil as well as orange blossom oil, neroli oil, orange peel oil and sandalwood oil.

Other traditional perfume substances that may be used within the scope of the present invention include, for example, the essential oils such as angelica root oil, anise oil, arnica blossom oil, sweet basil oil, bay oil, champaca blossom oil, silver fir oil, fir cone oil, elemi oil, eucalyptus oil, fennel oil, spruce needle oil, galbanum oil, geranium oil, ginger grass oil, guaiac wood oil, gurjun balsam oil, *helichrysum* oil, ho oil, ginger oil, iris oil, cajeput oil, calamus oil, chamomile oil, camphor oil, canaga oil, cardamom oil, *cassia* oil, pine needle oil, copaiba balsam oil, coriander oil, spearmint oil, caraway oil, cumin oil, lavender oil, lemon grass oil, lime oil, mandarin oil, lemon balm oil, ambrette seed oil, myrrh oil, clove oil, neroli oil, niaouli oil, olibanum oil, *origanum* oil, palmarosa oil, patchouli oil, Peru balsam oil, petitgrain oil, pepper oil, peppermint oil, allspice oil, pine oil, rose oil, rosemary oil, sandalwood oil, celery seed oil, spike lavender oil, star anise oil, turpentine oil, *thuja* oil, thyme oil, verbena oil, vetiver oil, juniper berry oil, vermouth oil, wintergreen oil, ylang-ylang oil, ysop oil, cinnamon oil, cinnamon leaf oil, citronella oil, lemon oil and cypress oil as well as ambrettolide, ambroxan, α-amylcinnamaldehyde, anethole, anise aldehyde, anise alcohol, anisole, anthranilic acid methyl ester, acetophenone, benzylacetone, benzaldehyde, benzoic acid ethyl ester, benzophenone, benzyl alcohol, benzyl acetate, benzyl benzoate, benzyl formate, benzyl valerate, borneol, bornyl acetate, boisambrene forte, α-bromostyrene, n-decylaldehyde, n-dodecylaldehyde, eugenol, eugenol methyl ether, eucalyptol, farnesol, fenchone, fenchyl acetate, geranyl acetate, geranyl formate, heliotropin, heptin carboxylic acid methyl ester, heptaldehyde, hydroquinone dimethyl ester, hydroxycinnamyl aldehyde, hydroxycinnamyl alcohol, indole, iron, isoeugenol, isoeugenol methyl ether, isosafrol, jasmine, camphor, carvacrol, carbon, p-cresol methyl ether, coumarin, p-methoxyacetophenone, methyl-n-amyl ketone, methyl anthranilic acid methyl ester, p-methylacetophenone, methyl chavicol, p-methylquinoline, methyl β-naphthyl ketone, methyl n-nonylaldehyde, nonyl alcohol, n-octylaldehyde, p-oxyacetphenone, pentadecanolide, β-phenylethyl alcohol, phenylacetaldehyde-dimethylacetal, phenylacetic acid, pulegon, safrole, salicylic acid isoamyl ester, salicylic acid methyl ester, salicylic acid hexyl ester, salicylic acid cyclohexyl ester, santalol, sandelice, skatol, terpineol, thyme, thymol, troenan, γ-undelactone, vanillin, veratrum aldehyde, cinnamyl aldehyde, cinnamyl alcohol, cinnamic acid, cinnamic acid ethyl ester, cinnamic acid benzyl ester, diphenyl oxide, limonene, linalool, linayl acetate and linalyl propionate, melusat, menthol, menthone, methyl-n-heptenone, pinene, phenyl acetaldehyde, terpinyl acetate, citral, citronellal and mixtures thereof.

The pro-fragrances are preferably used in detergents and cleaning agents, fabric softeners and cosmetics. These may be solid, gel or liquid formulations, and solid formulations may be in the form of powder, granules, tablets or tabs. Liquid formulations may be solutions, emulsions or dispersions.

Detergents may be used for manual or machine washing of textiles, in particular. They may be detergents or cleaning agents for industrial use or for the household area. Cleaning agents may be used for cleaning hard surfaces, for example. They may be dishwasher detergents, for example, which are used for manual or machine cleaning of dishes. They may also be conventional industrial or household cleaners with which hard surfaces such as furniture surfaces, flagstones, ceramic tiles, wall coverings and floor coverings are cleaned. Fabric softeners include, in particular, fabric softeners that are used for treating textiles during or after being laundered. The cosmetics may be pastes, ointments, creams, emulsions, lotions and solutions, in particular, alcohol-based solutions, which are known from fine perfumery, for example. The individual agents may be applied in any suitable form. For example, these may be agents to be applied by spraying. The inventive pro-fragrances may also be used to cover bad odors, which adhere well to solid surfaces when combined with other absorbents, for example.

The invention also relates to detergents or cleaning agents, fabric softeners or cosmetics which contain the inventive compounds or mixtures. The compounds or mixtures are used in an amount sufficient for the effect. Typically compounds of general formula (I) or mixtures containing them are used in amounts of less than 5 wt %, preferably less than 2 wt %, in particular, less than 1 wt %, in end formulations, i.e., ready-to-use detergents or cleaning agents, fabric softeners or cosmetics. Typical ingredient amounts are in the range of 0.05 to 0.5 wt %, in particular, 0.1 to 0.2 wt %. In fine perfumery it is also possible to work with high active ingredient concentrations of up to 40 wt % of scent substances.

Those skilled in the art are familiar with compositions of conventional detergents or cleaning agents, fabric softeners and cosmetics.

Detergents and cleaning agents and fabric softeners may contain other conventional ingredients of detergents and cleaning and fabric softeners, such as surfactants, builder substances, bleaching agents, other scent substances, enzymes and other active ingredients, but also disintegration aids, tablet disintegrants, to facilitate the disintegration of highly compressed tablets and tabs and to shorten the disintegration times. Surfactants, in particular, are among the essential ingredients of detergents and cleaning agents and fabric softeners.

The surfactant content will be selected to be higher or lower, depending on the intended use of the inventive agents. The surfactant content of detergents is usually between 10 and 40 wt %, preferably between 12.5 and 30 wt % and, in particular, between 15 and 25 wt %, whereas cleaning agents for dishwashing machines contained between 0.1 and 10 wt %, preferably between 0.5 and 7.5 wt % and, in particular, between 1 and 5 wt % surfactant, for example.

These surfactant substances originate from the group of anionic, nonionic, zwitterionic or cationic surfactants but for economic reasons and because of their performance spectrum, anionic surfactants are definitely preferred in washing and cleaning.

In principle, all anionic surfactant substances suitable for use on the human body may be used as the anionic surfactants here. These are characterized by a water-solubilizing anionic group, e.g., a carboxylate, sulfate, sulfonate or phosphate group and a lipophilic alkyl group with approx. 8 to 30 carbon atoms. In addition, glycol or polyglycol ether groups, ester, ether and amide groups as well as hydroxyl groups may be present in the molecule. Examples of suitable anionic surfactants include the following, each in the form of a sodium, potassium and/or ammonium salt, as well as the mono-, di- and trialkanolammonium salts with 2 to 4 carbon atoms in the alkanol group:

linear and branched fatty acids with 8 to 30 carbon atoms (soaps),
ether carboxylic acids of the formula $R^{13}$—O—$(CH_2$—$CH_2O)_x$—$CH_2$—COOH in which $R^{13}$ is a linear alkyl group with 8 to 30 carbon atoms and x=0 or 1 to 16,
alkylsarcosides with 8 to 24 carbon atoms in the acyl group,
acyltaurides with 8 to 24 carbon atoms in the acyl group,
acylsethionates with 8 to 24 carbon atoms in the acyl group,
sulfosuccinic acid monoalkyl and dialkyl esters with 8 to 24 carbon atoms in the alkyl group and sulfosuccinic acid monoalkylpolyoxyethyl esters with 8 to 24 carbon atoms in the alkyl group and 1 to 6 oxyethyl groups,
linear alkanesulfonates with 8 to 24 carbon atoms,
linear α-olefinsulfonate with 8 to 24 carbon atoms,
α-sulfofatty acid methyl esters of fatty acids with 8 to 30 carbon atoms,
alkyl sulfates and alkypolyglycol ether sulfates of the formula $R^{14}$—$O(CH_2$—$CH_2O)_x$—$OSO_3H$ in which $R^{14}$ is a preferably linear alkyl group with 8 to 30 carbon atoms and x=0 or 1 to 12,
mixed surfactant hydroxysulfonates,
sulfated hydroxyalkylpolyethylene and/or hydroxyalkylenepropylene glycol ethers,
sulfonated unsaturated fatty acids with 8 to 24 carbon atoms and 1 to 6 double bonds,
esters of tartaric acid and citric acid with alcohols which are addition products of approx. 2 to 15 molecules of ethylene oxide and/or propylene oxide onto fatty alcohols with 8 to 22 carbon atoms,
alkyl and/or alkenyl ether phosphates of the formula (E1-I)

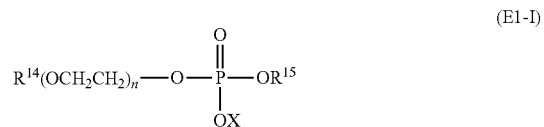

in which $R^{14}$ preferably stands for an aliphatic hydrocarbon radical with 8 to 30 carbon atoms, $R^{15}$ stands for hydrogen, a radical $(CH_2CH_2O)_n R^{16}$ or X, h stands for numbers from 1 to 10 and X stands for hydrogen, an alkali metal or an alkaline earth metal or $NR^{17}R^{18}R^{19}R^{20}$, where $R^{17}$ to $R^{19}$, independently of one another, stand for hydrogen or a $C_1$ to $C_4$ hydrocarbon radical,
sulfated fatty acid alkylene glycol esters of formula (E1-II)

in which $R^{20}CO$ stands for a linear or branched, aliphatic, saturated and/or unsaturated acyl radical with 6 to 22 carbon atoms, Alk stands for $CH_2CH_2$, $CHCH_3CH_2$ and/or $CH_2CHCH_3$, h stands for numbers from 0.5 to 5 and M stands for a cation,
monoglyceride sulfates and monoglyceride ether sulfates of formula (E1-III)

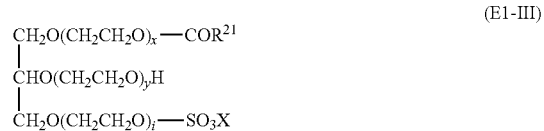

in which $R^{21}CO$ stands for a linear or branched acyl radical with 6 to 22 carbon atoms, x, y and i add up to 0 or stand for numbers from 1 to 30, preferably 2 to 10, and X stands for an alkali metal or an alkaline earth metal. Typical examples of monoglyceride (ether) sulfates suitable in the sense of the present invention include the reaction products of lauric acid monoglyceride, coconut fatty acid monoglyceride, palmitic acid monoglyceride, stearic acid monoglyceride, oleic acid monoglyceride and tallow fatty acid monoglyceride as well as their ethylene oxide adducts with sulfur trioxide or chlorosulfonic acid in the form of their sodium salts. Monoglyceride sulfates of formula (E1-III) are preferably used in which $R^{21}CO$ stands for a linear acyl radical with 8 to 18 carbon atoms:

amide ether carboxylic acids,
condensation products of $C_8$-$C_{30}$ fatty alcohols with protein hydrolysates and/or amino acids and their derivatives with which those skilled in the art are familiar as protein-fatty acid condensates such as Lamepon® grades, Gluadin® grades, Hostapon® KCG or the Amisoft® grades.

Preferred anionic surfactants include alkyl sulfates, alkylpolyglycol ether sulfates and ether carboxylic acids with 10 to 18 carbon atoms in the alkyl group and up to 12 glycol ether groups in the molecule, sulfosuccinic acid monoalkyl and dialkyl esters with 8 to 18 carbon atoms in the alkyl group and sulfosuccinic acid monoalkylpolyoxyethyl esters with 8 to 18 carbon atoms in the alkyl group and 1 to 6 oxyethyl groups, monoglyceride sulfates, alkyl and alkenyl ether phosphates and protein-fatty acid condensates.

Cationic surfactants may also be used. Preferred according to this invention are cationic surfactants of the quaternary ammonium compound type, ester quats and amidoamines. Preferred quaternary ammonium compounds include ammonium halides, in particular, chlorides and bromides such as alkyltrimethylammonium chlorides, dialkyldimethylammonium chlorides and trialkylmethylammonium chloride, e.g., cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, lauryldimethylammonium chloride, lauryldimethylbenzylammonium chloride and tricetylmethylammonium chloride as well as the imidazolium compounds known by the INCI designations quaternium-27 and quaternium-83 are preferred. The long alkyl chains of the surfactants mentioned above preferably have 10 to 18 carbon atoms.

Ester quats are known substances which contain at least one ester function as well as at least one quaternary ammonium group as a structural element. Preferred ester quats are quaternated ester salts of fatty acids with triethanolamine, quaternated ester salts of fatty acids with diethanolalkylamines and quaternated ester salts of fatty acids with 1,2-dihydroxypropyldialkylamines. Such products are distributed under the brand names Stepantex®, Dehyquart® and Armocare®, for example. The products Armocare® VGH-70, and N,N-bis(2-palmitoyloxyethyl)dimethylammonium chloride as well as Dehyquart® F-17, Dehyquart® C-4046, Dehyquart® L80 and Dehyquart® AU-35 are examples of such ester quats.

The alkylamidoamines are usually prepared by amidation of natural or synthetic fatty acids and fatty acid cuts with dialkylaminoamines. Stearamidopropyldimethylamine, which is available commercially under the brand name Tegoamid® S18 is an especially suitable compound from the substance group according to this invention.

The cationic surfactants are preferably present in the inventive agents in amounts of 0.05 to 10 wt %, based on the total application preparation. Amounts of 0.1 to 5 wt % are especially preferred.

In addition to or instead of the cationic surfactants, the agents may also contain other surfactants or emulsifiers, in principle, both anionic and ampholytic and nonionic surfactants as well as all types of known emulsifiers being suitable. The group of ampholytic or amphoteric surfactants comprises zwitterionic surfactants and ampholytes. The surfactants may already have an emulsifying effect.

Zwitterionic surfactants are surfactant compounds having at least one quaternary ammonium group and at least one —$COO^{(-)}$ or —$SO_3^{(-)}$ group in the molecule. Especially suitable zwitterionic surfactants include the betaines such as N-alkyl-N,N-dimethylammonium glycinates, e.g., the coconut alkyldimethylammonium glycinate, N-acylaminopropyl-N,N-dimethylammonium glycinates, e.g., coconut acylaminopropyldimethylammonium glycinate and 2-alkyl-3-carboxymethyl-3-hydroxyethylimidazolines with 8 to 18 carbon atoms each in the alkyl or acyl group as well as coconut acylaminoethylhydroxyethylcarboxymethyl glycinate. A preferred zwitterionic surfactant is the fatty acid amide derivative known by the INCI name cocamidopropyl betaine.

Ampholytes are understood to be surfactant compounds which have, in addition to a $C_8$-$C_{24}$ alkyl or acyl group in the molecule, at least one free amino group and at least one —COOH or —$SO_3H$ group and are capable of forming internal salts. Examples of suitable ampholytes include N-alkylglycines, N-alkylpropionic acids, N-alkylaminobutyric acids, N-alkyliminodipropionic acids, N-hydroxyethyl-N-alkylamidopropylglycines, N-alkyltaurines, N-alkyl-sarcosines, 2-alkylaminopropionic acids and alkylaminoacetic acids each with approx. 8 to 24 carbon atoms in the alkyl group. Especially preferred ampholytes include N-coconut alkylaminopropionate, coconut acylaminoethylaminopropionate and $C_{12}$-$C_{18}$ acylsarcosine.

Nonionic surfactants contain as the hydrophilic group, e.g., a polyol group, a polyalkylene glycol ether group or a combination of a polyol group and a polyglycol ether group. Such compounds include, for example:

addition products of 2 to 50 mol ethylene oxide and/or 1 to 5 mol propylene oxide onto linear and branched fatty alcohols with 8 to 30 carbon atoms, onto fatty acid with 8 to 30 carbon atoms and onto alkylphenols with 8 to 15 carbon atoms in the alkyl group, with a methyl- or $C_2$-$C_6$ alkyl radical end group capped addition products of 2 to 50 mol ethylene oxide and/or 1 to 5 mol propylene oxide onto linear and branched fatty alcohols with 8 to 30 carbon atoms, onto fatty acids with 8 to 30 carbon atoms and onto alkylphenols with 8 to 15 carbon atoms in the alkyl group such as the grades available under the brand names Dehydol® LS, Dehydol® LT (Cognis), $C_{12}$-$C_{30}$ fatty acid mono- and diesters of addition products of 1 to 30 mol ethylene oxide onto glycerol, addition products of 5 to 60 mol ethylene oxide onto castor oil and hardened castor oil, polyol fatty acid esters such as the commercial product Hydagen® HSP (Cognis) or Sovermol grades (Cognis), alkoxylated triglycerides, alkoxylated fatty acid alkyl esters of formula (E4-I)

$$R^{22}CO\text{—}(OCH_2CHR^{23})_w OR^{24} \qquad (E4\text{-}I)$$

in which $R^{22}CO$ stands for a linear or branched, saturated and/or unsaturated acyl radical with 6 to 22 carbon atoms, $R^{23}$ stands for hydrogen or methyl, $R^{24}$ stands for linear or branched alkyl radicals with 1 to 4 carbon atoms and w stands for numbers from 1 to 20, amine oxides, hydroxy mixed ethers, sorbitan fatty acid esters and addition products of ethylene oxide onto sorbitan fatty acid esters such as the polysorbates, sugar fatty acid esters and addition products of ethylene oxide onto sugar fatty acid esters, addition products of ethylene oxide onto fatty acid alkanolamides and fatty amines, sugar surfactants of the alkyl and alkenyl oligoglycoside type according to formula (E4-II)

in which $R^{25}$ stands for an alkyl or alkenyl radical with 4 to 22 carbon atoms, G stands for a sugar radical with 5 or 6 carbon atoms and p stands for numbers from 1 to 10. They may be obtained according to the relevant methods or preparative organic chemistry. The alkyl and alkenyl oligoglycosides may be derived from aldoses and/or ketoses with 5 or 6 carbon atoms, preferably glucose. The preferred alkyl and/or alkenyl oligoglycosides are thus alkyl and alkenyl oligoglucosides. The index number p in the general formula (E4-II) denotes the degree of oligomerization (DP), i.e., the distribution of mono- and oligoglycosides, and stands for a number between 1 and 10. Whereas p in the individual molecule must always be an integer and may assume values of p=1 to 6, in particular, the value p for a certain alkyl oligoglycoside is a mathematical quantity obtained analytically and usually representing a fraction. Alkyl and/or alkenyl oligoglycosides with an average degree of oligomerization p of 1.1 to 3.0 are preferably used. From the standpoint of technical applications, alkyl and/or alkenyl oligoglycosides whose degree of oligomerization is less than 1.7 and, in particular, between 1.2 and 1.4 are preferred. The alkyl and/or alkenyl radical $R^{25}$ may be derived from primary alcohols with 4 to 11 carbon atoms, preferably 8 to 10 carbon atoms. Typical examples include butanol, caproic alcohol, caprylic alcohol, capric alcohol and undecyl alcohol as well as their technical-grade mixtures such as those obtained, e.g., in hydrogenation of technical-grade fatty acid methyl esters or in the course of hydrogenation of aldehydes from the Roelen oxo synthesis. Alkyl oligoglucosides with a chain length of $C_8$-$C_{10}$ (DP=1 to 3), which are obtained as the initial fraction in distillative separation of technical-grade $C_8$-$C_{18}$ coconut fatty alcohol and which may be contaminated with an amount of less 6 wt % $C_{12}$ alcohol, as well as alkyl oligoglucosides based on technical-grade $C_{9/11}$ oxo alcohols (DP=1 to 3) are preferred. The alkyl and/or alkenyl radical $R^{25}$ may also be derived from primary alcohols with 12 to 22 carbon atoms, preferably 12 to 14 carbon atoms. Typical examples include lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol as well as their technical-grade mixtures which are obtained by the method described above. Alkyl oligoglucosides based on hardened $C_{12/14}$ coconut alcohol with a DP of 1 to 3 are preferred.

Sugar surfactants of the fatty acid N-alkylpolyhydroxyalkylamide type, a nonionic surfactant of the formula (E4-III)

in which $R^{26}CO$ stands for an aliphatic acyl radical with 6 to 22 carbon atoms, $R^{27}$ stands for hydrogen, an alkyl or hydroxyalkyl radical with 1 to 4 carbon atoms and [Z] stands for a linear or branched polyhydroxyalkyl radical with 3 to 12 carbon atoms and 3 to 10 hydroxyl groups. The fatty acid N-alkylpolyhydroxyalkylamides are known substances which can usually be obtained by reductive amination of a reducing sugar with ammonia, an alkylamine or an alkanolamine and subsequent acylation with a fatty acid, a fatty acid alkyl ester or a fatty acid chloride. The fatty acid N-alkylpolyhydroxyalkylamides are preferably derived from reducing sugars with 5 or 6 carbon atoms, in particular glucose. The preferred fatty acid N-alkylpolyhydroxyalkylamides are therefore fatty acid N-alkylglucamides such as those represented by formula (E4-IV):

The fatty acid N-alkylpolyhydroxyalkylamides used are preferably glucamides of the formula (E4-IV) in which $R^{29}$ stands for hydrogen or an alkyl group and $R^{28}CO$ stands for an acyl group of caproic acid, caprylic acid, capric acid, lauric acid, myristic acid, palmitic acid, palmoleic acid, stearic acid, isostearic acid, oleic acid, elaidic acid, petroselinic acid, linoleic acid, linolenic acid, arachic acid, gadoleic acid, behenic acid or erucaic acid and/or technical-grade mixtures of these acids. Especially preferred fatty acid N-alkylglucamides are those of formula (E4-IV) that are obtained by reductive amination of glucose with methylamine and then acylation with lauric acid or $C_{12/14}$ coconut fatty acid and/or a corresponding derivative. In addition, the polyhydroxyalkylamides may also be derived from maltose and palatinose.

Preferred nonionic surfactants have proven to be the alkylene oxide addition products onto saturated linear fatty alcohols and fatty acids each with 2 to 30 mol ethylene oxide per mol fatty alcohol and/or fatty acid. Preparations with excellent properties are also obtained when they contain fatty acid esters of ethoxylated glycerol as the nonionic surfactants.

These compounds are characterized by the following parameters. The alkyl radical contains 6 to 22 carbon atoms and may be both linear and branched. Primary linear aliphatic radicals and those with methyl branching in position 2 are preferred. Such alkyl radicals preferably include 1-octyl, 1-decyl, 1-lauryl, 1-myristyl, 1-cetyl and 1-stearyl. Especially preferred are 1-octyl, 1-decyl, 1-lauryl, 1-myristyl. When using "oxo alcohols" as the starting materials, compounds with an odd number of carbon atoms in the alkyl chain are predominant.

In addition, the sugar surfactants may also be used as nonionic surfactants. These are preferably used in amounts of 0.1 to 20 wt %, based on the respective total composition. Amounts of 0.5 to 15 wt % are especially preferred and amounts of 0.5 to 7.5 wt % are most especially preferred.

The compounds with alkyl groups that are used as the surfactant may be uniform substances. However, it is preferable as a rule to start with native plant or animal raw materials in the production of these substances, so that substance mixtures with different alkyl chain lengths are obtained, depending on the respective raw material.

The surfactants, which are addition products of ethylene oxide and/or propylene oxide onto fatty alcohols or derivatives of these addition products, may be products with a "normal" homolog distribution as well as those with a narrow homolog distribution. A "normal" homolog distribution is understood to refer to mixtures of homologs that are obtained by reacting fatty alcohol and alkylene oxide using alkali metals, alkali metal hydroxides or alkali metal alcoholates as catalysts. Narrow homolog distributions, however, are obtained when using, for example, hydrotalcite, alkaline earth metal salts of ether carboxylic acids, alkaline earth metal oxides, hydroxides or alcoholates as catalysts. The use of products with a narrow homolog distribution may be preferred.

The additional surfactants are usually used in amounts of 0.1 to 45 wt %, preferably 0.5 to 30 wt % and most especially preferably from 0.5 to 25 wt %, each based on the respective total composition. The amount used depends essentially on the intended purpose of the inventive agent. If it is a shampoo or another cleaning agent, surfactant amounts of more than 45 wt % are customary.

These agents may also contain at least one emulsifier. Emulsifiers cause the formation of water-stable and/or oil-stable adsorption layers at the phase boundary, protecting the dispersed droplets from coalescence and thereby stabilizing the emulsion. Emulsifiers are therefore composed of a hydrophobic molecule part and a hydrophilic molecule part, like surfactants. Hydrophilic emulsifiers preferably form O/W emulsions and hydrophobic emulsifiers preferably form W/O emulsions. The choice of these emulsifying surfactants or emulsifiers will depend on the substances to be dispersed and the particular external phase, as well as how finely divided the emulsion is. Emulsifiers that can be used according to this invention include, for example:

- addition products of 4 to 100 mol ethylene oxide and 1 to 5 mol propylene oxide onto linear fatty alcohols with 8 to 22 carbon atoms onto fatty acids with 12 to 22 carbon atoms and onto alkylphenols with 8 to 15 carbon atoms in the alkyl group,
- $C_{12}$-$C_{22}$ fatty acid mono- and diesters of addition products of 1 to 30 mol ethylene oxide onto polyols with 3 to 6 carbon atoms, in particular onto glycerol,
- ethylene oxide and polyglycerol addition products onto methyl glucoside fatty acid
- esters, fatty acid alkanolamides and fatty acid glucamides,
- $C_8$-$C_{22}$ alkylmono- and oligoglycosides and their ethoxylated analogs, whereby oligomerization degrees of 1.1 to 5, in particular 1.2 to 2.0 and glucose as the sugar component are preferred,
- mixtures of alkyl(oligo)glucosides and fatty alcohols, e.g., the commercially available product Montanov® 68,
- addition products of 5 to 60 mol ethylene oxide onto castor oil and hardened castor oil,
- partial esters of polyols with 3 to 6 carbon atoms with saturated fatty acids with 8 to 22 carbon atoms,
- sterols; sterols are understood to be a group of steroids which have a hydroxyl group on carbon 3 of the steroid structure and are isolated from both animal tissue (zoosterols) and vegetable fats (phytosterols). Examples of zoosterols include cholesterol and lanosterol. Examples of suitable phytosterols include ergosterol, stigmasterol and sitosterol. Sterols and mycosterols are also isolated from fungi and yeasts.
- phospholipids; these include especially the glucose phospholipids, which are obtained, e.g., as lecithins and/or phosphatidylcholines from egg yolk or plant seeds (e.g., soybeans), for example,
- fatty acid esters of sugars and sugar alcohols such as sorbitol,
- polyglycerols and polyglycerol derivatives such as polyglycerol, poly-12-hydroxystearat(commercial product Dehymuls® PGPH),
- linear and branched fatty acids with 8 to 30 carbon atoms and their Na, K, ammonium, Ca, Mg and Zn salts.

The emulsifiers are preferably used in amounts of 0.1 to 25 wt %, in particular 0.1 to 3 wt %, based on the respective total composition.

Another important group of fabric softener ingredients, detergent and cleaning agent ingredients is the builder substances. This substance class is understood to include both organic and inorganic builder substances. These are compounds that can have a carrier function in the inventive agents as well as acting as a water softener substance in use.

Suitable builders include, for example, alkali metal gluconates, citrates, nitrilotriacetate, carbonates and bicarbonates, in particular, sodium gluconate, citrate and nitrilotriacetate as well as sodium and potassium carbonate and bicarbonate and alkali metal hydroxides and alkaline earth metal hydroxides, in particular sodium and potassium hydroxide, ammonium and amines, in particular, mono- and triethanolamine and/or mixtures thereof. These also include the salts of glutaric acid, succinic acid, adipic acid, tartaric acid and benzenehexacarboxylic acid as well as phosphonates and phosphates.

Usable organic builder substances include, for example, the polycarboxylic acids that may be used in the form of their sodium salts, where polycarboxylic acids are understood to include those carboxylic acids having more than one acid function. For example, these include citric acid, adipic acid, succinic acid, glutaric acid, malic acid, tartaric acid, maleic acid, fumaric acid, sugar acids, aminocarboxylic acids, nitrilotriacetic acid (NTA), if such a use is not objectionable for ecological reasons, as well as mixtures thereof. Preferred salts include the salts of polycarboxylic acids such as citric acid, adipic acid, succinic acid, glutaric acid, tartaric acid, sugar acids and mixtures thereof. The acids per se may also be used. In addition to their builder effect, the acids typically also have the property of an acidifying component and thus also serve to adjust a lower and milder pH of detergents or cleaning agents, as in the inventive granules, for example. Citric acid, succinic acid, glutaric acid, adipic acid, gluconic acid and any mixtures thereof may be mentioned here, in particular.

Also polymeric polycarboxylates are suitable as builders, including the alkali metal salts of polyacrylic acid or polymethacrylic acid, e.g., those with a relative molecular weight of 500 g/mol to 70,000 g/mol. The (co)polymeric polycarboxylates may be used either as a powder or as an aqueous solution. The (co)polymeric polycarboxylate content of the agents is preferably 0.5 to 20 wt %, in particular, 3 to 10 wt %.

To improve the water solubility, the polymers may also contain allylsulfonic acid, allyloxybenzenesulfonic acid and methallylsulfonic acid as monomers. Biogradable polymers of more than two different monomer units, e.g., those containing as monomer salts of acrylic acid and maleic acid as well as vinyl alcohol and/or vinyl alcohol derivatives or containing as monomers salts of acrylic acid and 2-alkylallylsulfonic acid as well as sugar derivatives are preferred, in particular. Other preferred copolymers include those having as monomers preferably acrolein and acrylic acid/acrylic acid salts and/or acrolein and vinyl acetate. Likewise, polymeric aminodicarboxylic acids, their salts or their precursor substances are also to be mentioned as additional preferred builder substances. Polyaspartic acids and/or their salts and derivatives which also have a bleach-stabilizing effect in addition to co-builder properties are especially preferred.

Other suitable builder substances include polyacetals, which may be obtained by reacting dialdehydes with polycarboxylic acids having 5 to 7 carbon atoms and at least three hydroxyl groups. Preferred polyacetals are obtained from dialdehydes such as glyoxal, glutaraldehyde, terephthalaldehyde and mixtures thereof and from polycarboxylic acids such as gluconic acid and/or glucoheptonic acid.

Other suitable organic builder substances include dextrins, e.g., oligomers and/or polymers of carbohydrates which can be obtained by partial hydrolysis of starches. The hydrolysis may be performed according to conventional methods, e.g., acid- or enzyme-catalyzed methods. These are preferably hydrolysis products with average molecular weights in the range of 400 to 500,000 g/mol. A polysaccharide with a dextrose equivalent (DE) in the range of 0.5 to 40, in particular, 2 to 30, is preferred, where DE is a conventional measure of the reducing effect of a polysaccharide in comparison with dextrose, which has a DE of 100. Maltodextrins with a DE between 3 and 20 and dry glucose syrups with a DE between 20 and 30 as well as yellow dextrins and white dextrins with higher molecular weights in the range of 2,000 to 30,000 may be used. The oxidized derivatives of such dextrins are their reaction products with oxidizing agents which are capable of oxidizing at least one alcohol function of the saccharide ring to the carboxylic acid function.

Oxydisuccinates and other derivatives of disuccinates, preferably ethylenediaminedisuccinate, are also suitable co-builders. Ethylenediamine-N,N'-disuccinate (EDDS) is preferably used in the form of its sodium or magnesium salts. Also preferred in this context are glycerol disuccinates and glycerol trisuccinates. Suitable amounts for use in formulations containing zeolite and/or silicate are from 3 to 15 wt %.

Other organic co-builders that may also be used include, for example, acetylated hydroxycarboxylic acids and/or the salts thereof, which may also be in lactone form and which have at least four carbon atoms and at least one hydroxyl group plus max. two acid groups.

Another substance class with co-builder properties are the phosphonates. These are, in particular, hydroxyalkanephosphonates and/or aminoalkanephosphonates. Of the hydroxyalkanephosphonates, 1-hydroxyethane-1,1-diphosphonate (HEDP) is especially important as a co-builder. It is preferably used as a sodium salt, whereby the disodium salt gives a neutral reaction and the tetrasodium salt gives an alkaline reaction (pH 9). Preferably ethylenediaminetetramethylenephosphonate (EDTMP), diethylenetriamine-pentamethylenephosphonate (DTPMP) and their higher homologs may be used as the aminoalkanephosphonates. They are preferably used in the form of the neutral reacting sodium salts, e.g., as hexasodium salt of EDTMP and/or as hepta- and octasodium salts of DTPMP. From the class of phosphonates, HEDP is preferably used as a builder.

The aminoalkanephosphonates also have a marked heavy metal binding capacity. Accordingly, in particular when the agents also contain bleaches, it may be preferable to use aminoalkane-phosphonates, in particular, DTPMP, or mixtures of the aforementioned phosphonates.

In addition, all compounds capable of forming complexes with alkaline earth ions may also be used as co-builders.

A preferred inorganic builder is a finely crystalline synthetic zeolite containing bound water. The finely crystalline synthetic zeolite containing bound water used here is preferably zeolite A and/or P. For example, zeolite MAP, e.g., Doucil A24® (commercial product of the company Crosfield) is used as zeolite P. However, zeolite X and mixtures of A, X and/or P, e.g., a co-crystal product of the zeolites A and X, Vegobond® AX (commercial product of Condea August S.p.A.) are also suitable. The zeolite may be used as a spray-dried powder or as an undried stabilized emulsion, which is still moist from its preparation. For the case when the zeolite is used as a suspension, it may contain small added amounts of nonionic surfactants as stabilizer, e.g., 1 to 3 wt % based on zeolite, of ethoxylated $C_{12}$-$C_{18}$ fatty alcohols with two to five ethylene oxide groups, $C_{12}$-$C_{14}$ fatty alcohols with four to five ethylene oxide groups or ethoxylated isotridecanols. Suitable zeolites have an average particle size of less than 10 μM (volume distribution; measurement method: Coulter counter) and preferably contain 18 to 22 wt %, in particular, 20 to 22 wt % bound water. In preferred embodiments, zeolites are present in the premix in amounts of 10 to 94.5 wt %, but it may be especially preferred if zeolites are present in amounts of 20 to 70 wt %, in particular 30 to 60 wt %.

Suitable partial substitutes for zeolites include sheet silicates of natural and synthetic origin. Their usability is not limited to a specific composition and/or structural formula. However, smectites, in particular bentonites, are preferred here. Crystalline sheet sodium silicates of the general formula $NaMSi_xO_{2x+1} \cdot yH_2O$, where M denotes sodium or hydrogen, x denotes a number from 1.9 to 4 and y denotes a number from 0 to 20 and preferred values for x are 2, 3 or 4 are suitable for substitution of zeolites or phosphates. Preferred crystalline sheet silicates of the given formula include those in which M stands for sodium and x assumes values of 2 or 3. In particular, both β- and δ-sodium disilicates $Na_2Si_2O_5 \cdot yH_2O$ are preferred.

It is also possible to use the generally known phosphates as builder substances if such a use should not be avoided for ecological reasons. In particular, the sodium salts of orthophosphates, pyrophosphates and, in particular, tripolyphosphates are suitable.

The agents contain builders preferably in amounts, based on the composition, of 0 to 20 wt % preferably 0.01 to 12 wt %, in particular, 0.1 to 8 wt %, extremely preferably, 0.3 to 5 wt %.

In addition to the ingredients already listed, the inventive detergents and cleaning agents may additionally contain one or more substances from the group of bleaching agents, bleach activators, enzymes, pH adjusting agents, fluorescent agents, dyes, foam inhibitors, silicone oils, anti-redeposition agents, optical brighteners, graying inhibitors, dye transfer inhibitors, corrosion inhibitors and silver protectants. These substances are described below.

Of the compounds that yield $H_2O_2$ in water and serve as bleaching agents, sodium perborate tetrahydrate, sodium perborate monohydrate and sodium percarbonate are especially important. Other bleaching agents that may be used include, for example, peroxypyrophosphates, citrate perhydrates and peracid salts or peracids that supply $H_2O_2$ such as perbenzoates, peroxophthalates, diperazelaic acid, phthaloimino peracid or diperdodecanedioic acid. When using bleaching agents, it is also possible to omit the use of surfactants and/or builders, so that pure bleaching agent tablets can be produced. If such bleaching agent tablets are to be used for washing laundry, then a combination of sodium percarbonate with sodium sesquicarbonate is preferred, regardless of which additional ingredients are present in the molded bodies. If cleaning agents or bleaching agent tablets are produced for machine dishwashing, bleaching agents from the group of organic bleaching agents may also be used. Typical organic bleaching agents include the diacyl peroxides, e.g., dibenzoyl peroxide. Other typical organic bleaching agents include the peroxy acids, where the alkylperoxy acids and arylperoxy acids may be mentioned, in particular, as examples. Preferred representatives include (a) peroxybenzoic acid and its ring-substituted derivatives, such as alkylperoxybenzoic acids as well as peroxy-α-naphthoic acid and magnesium monoperphthalate, (b) the aliphatic or substituted aliphatic peroxy acids such as peroxylauric acid, peroxystearic acid, ε-phthalimidoperoxycaproic acid (phthaloiminoperoxyhexanoic acid (PAP)), o-carboxybenzamidoperoxycaproic acid, N-nonenylamidoperadipic acid and N-nonenylamidopersuccinates and (c) aliphatic and araliphatic peroxydicarboxylic acids such as 1,12-diperoxyphthalic acid, 1,9-diperoxyazelaic acid, diperoxysebacic acid, diperoxybrassylic acid, diperoxyphthalic acids, 2-decyldiperoxybutane-1,4-diacid, N,N-terephthaloyldi-(6-aminopercaproic acid) may also be used.

Substances that release chlorine or bromine may also be used as bleaching agents in agents for machine dishwashing. Of the suitable materials that release chlorine or bromine, heterocyclic N-bromo and N-chloroamides may be considered, e.g., trichloroisocyanuric acid, tribromoisocyanuric acid, dibromoisocyanuric acid and/or dichloroisocyanuric acid (DICA) and/or the salts thereof with cations such as potassium and sodium. Hydantoin compounds such as 1,3-dichloro-5,5-dimethylhydantoin are also suitable.

To achieve an improved bleaching effect when washing or cleaning at temperatures of 60° C. or lower, bleach activators may also be incorporated into the inventive detergents and cleaning agents. Bleach activators may include compounds that yield aliphatic peroxocarboxylic acids with preferably 1 to 10 carbon atoms, in particular, 2 to 4 carbon atoms and/or optionally substituted perbenzoic acid under perhydrolysis conditions may be used as bleach activators. Substances that have O-acyl groups and/or N-acyl groups with the aforementioned number of carbon atoms and/or optionally substituted benzoyl groups are suitable. Polyacylated alkylenediamines, in particular, tetraacetylethylenediamine (TAED), acylated triazine derivatives, in particular, 1,5-diacetyl-2,4-dioxohexahydro-1,3,5-triazine (DAD HT), acylated glycolurils, in particular, tetraacetylglycoluril (TAGU), N-acylimide, in particular, N-nonanoylsuccinimide (NOSI), acylated phenolsulfonates, in particular, n-nonanoyl- or isononanoyloxybenzene sulfonate (n- and/or iso-NOBS), carboxylic anhydride, in particular, phthalic anhydride, acylated polyvalent alcohols, in particular, triacetin, ethylene glycol diacetate and 2,5-diacetoxy-2,5-dihydrofuran are preferred.

In addition to or in place of the conventional bleach activators, bleach catalysts may also be present. These substances are bleach-potentiating transition metal salts and/or transition metal complexes, e.g., Mn, Fe, Co, Ru or Mo saline complexes or carbonyl complexes. Mn, Fe, Co, Ru, Mo, Ti, V and Cu complexes with tripod ligands containing N as well as Co, Fe, Cu and Ru-ammine complexes may also be used as bleach catalysts.

The enzymes that may be used include those from the class of proteases, lipases, amylases, cellulases and/or mixtures thereof. Enzymatic active ingredients obtained from bacterial strains or fungi, e.g., *Bacillus subtilis, Bacillus licheniformis* and *Streptomyces griseus* are especially suitable. Proteases of the subtilisin type and, in particular, proteases obtained from *Bacillus lentus* are preferably used. Enzyme mixtures, e.g., from protease and amylase or protease and lipase or protease and lipase or protease and cellulase or from cellulase and lipase or from protease, amylase and lipase or protease, lipase and cellulase, but in particular mixtures containing cellulase are of special interest. Peroxidases or oxidases have also proven suitable in some cases. The enzymes may be adsorbed onto carrier substances and/or embedded in sheathing substances to protect them from premature decomposition. The amount of enzymes, enzyme mixtures or enzyme granules in the inventive molded bodies may be approx. 0.1 to 5 wt %, preferably 0.1 to approx. 2 wt %, for example. The most commonly used enzymes include lipases, amylases, cellulases and proteases. Preferred proteases include BLAP® 140 from the company Biozym, Optimase® M-440 and Opticlean® M-250 from the company Solvay Enzymes; Maxacal® CX and Maxapem® or Esperase® from the company Gist Brocades or Savinase® from the company Novo. Especially suitable cellulases and lipases include Celluzym® 0.7 T and Lipolase® 30 T from the company Novo Nordisk. Duramyl® and Termamyl® 60 T and Termamyl® 90 T from the company Novo, Amylase-LT® from the company Solvay Enzymes or Maxamyl® P5000 from the company Gist Brocades are used, in particular. Other enzymes may also be used.

In addition, the detergents and cleaning agents may also contain components which have a positive influence on the release of oil and fat from textiles (soil repellents). This effect becomes especially pronounced when a textile that has already been washed repeatedly with an inventive detergent containing this oil- and fat-releasing component is soiled. The preferred oil- and fat-releasing components include, for example, nonionic cellulose ethers such as methyl cellulose and methyl hydroxypropyl cellulose with a methoxyl group content of 15 to 30 wt % and a hydroxypropoxyl group content of 1 to 15 wt %, each based on the nonionic cellulose ether, as well as the polymers of phthalic acid and/or terephthalic acid known from the state of the art and/or their derivatives, in particular, polymers of ethylene terephthalates and polyethylene glycol terephthalates or anionically and/or nonionically modified derivatives thereof. Of these, the sulfonated derivatives of phthalic acid polymers and terephthalic acid polymers are especially preferred.

In addition, the agents may also contain as optical brighteners derivatives of diaminestilbenedisulfonic acid and/or its alkali metal salts. For example, the salts of 4,4'-bis(2-anilino-4-morpholino-1,3,5-triazinyl-6-amino)stilbene-2,2'-disulfonic acid or similarly constructed compounds which have a diethanolamino group, a methylamino group, an anilino group or a 2-methoxyethylamino group instead of the morpholino group are also suitable. In addition, brighteners of the substituted diphenylstyryl type may also be present, e.g., the alkali salts of 4,4'-bis(2-sulfostyryl)diphenyl, 4,4'-bis(4-chloro-3-sulfostyryl)diphenyl or 4-(4-chlorostyryl)-4'-(2-sulfostyryl)diphenyl. Mixtures of the aforementioned brighteners may also be used.

To improve the aesthetic impression of the inventive agents, they may be pigmented with suitable dyes. Preferred dyes, the selection of which will not pose any problems for those skilled in the art, have a high stability in storage and are insensitive to the other ingredients of the agents and to light, and do not have any pronounced substantivity with respect to textile fibers, so as not to stain the latter.

According to this invention, detergents and cleaning agents also include dishwashing agents. The inventive dishwashing agents may contain corrosion inhibitors to protect the washed utensils or the machine, whereby, in particular, silver protectants have a special importance in the field of machine dishwashing. In general, silver protectants selected from the group of triazoles, benzotriazoles, bisbenzotriazoles, aminotriazoles, alkylaminotriazoles and transition metal salts or complexes may be used, in particular. Benzotriazole and/or alkylaminotriazole are especially preferred for use. In addition, cleaning agent formulations frequently also contain agents having active chlorine which can significantly reduce corrosion on the surface of silver. In chlorine-free cleaners, oxygen-containing and nitrogen-containing organic redox-active compounds are used in particular, such as divalent and trivalent phenols, e.g., hydroquinone, pyrocatechol, hydroxyhydroquinone, gallic acid, phloroglucine, pyrogallol and/or derivatives of these classes of compounds. Salt-like and complex-like inorganic compounds, e.g., the salts of the metals Mn, Ti, Zr, Hf, V, Co and Ce are frequently also used. Transition metal salts selected from the group of manganese and/or cobalt salts and/or complexes are preferred here, especially preferably the cobalt-(ammine) complexes, the cobalt-(acetate) complexes, the cobalt-(carbonyl) complexes, the chlorides of cobalt or manganese and of manganese sulfate. Likewise, zinc compounds may be used to prevent corrosion of the washed utensils.

Special ingredients that may be used in the inventive agents for machine dishwashing or for cleaning hard surfaces include substances to prevent re-soiling of surfaces and/or to facilitate the release of dirt after a single use ("soil-release compounds").

The soil-release compounds that may be used include all those compounds known in the state of the art. Especially suitable examples include cationic polymers, e.g., hydroxypropyltrimethylammonium guar, copolymers of aminoethyl methacrylate and acrylamide as well as copolymers of dimethyldiallylammonium chloride and acrylamide, polymers with imino groups, cationic cellulose derivatives, cationic homopolymers and/or copolymers (monomer units: quaternated ammonium alkyl methacrylate groups).

The cationic polymers are especially preferably selected from cationic polymers of copolymers of monomers such as trialkylammonium alkyl (meth)acrylate and/or acrylamide; dialkyldiallyldiammonium salts; polymer-like reaction products of ethers or esters of polysaccharides with ammonium side groups, in particular, guar derivatives, cellulose derivatives and starch derivatives; polyadducts of ethylene oxide with ammonium groups; quaternary ethyleneimine polymers and polyesters and polyamides with quaternary side groups as soil-release compounds. Natural polyuronic acids and related substances as well as polyampholytes and hydrophobized polyamopholytes and/or mixtures of these substances are also extremely preferred within the scope of this patent application.

This list of ingredients of fabric softeners and detergents and cleaning agents is by no means comprehensive but instead merely gives the most essential typical ingredients of such agents. In particular, inasmuch as they are liquid or gel preparations, these agents may also contain organic solvents. These are preferably monovalent or polyvalent alcohols with 1 to 4 carbon atoms. Preferred alcohols in such agents include ethanol, 1,2-propanediol, glycerol as well as mixtures of these alcohols. In preferred embodiments, such agents contain 2 to 12 wt % of such alcohols.

Essentially the agents may have different physical states. In another preferred embodiment, the fabric softeners, detergents or cleaning agents are liquid or gel agents, in particular, liquid detergents or liquid dishwashing detergents or cleaning gels, and they may, in particular, also be cleaning agents in the form of gels for cleaning toilets.

These are preferably intrinsically viscous cleaning agents in the form of gels with a viscosity of 30,000-150,000 mPas, containing as the gelatinizing agent a polysaccharide, as the emulsifier and wetting-active component a $C_{8-10}$ alkyl polyglycoside or $C_{12-14}$ alkyl polyglycoside and perfume oil. Fatty alcohol ether sulfates (FAEOS) and fatty alcohol sulfates (FAS) may also be present as additional co-surfactants. The ratio of APG to co-surfactant is then usually greater than 1, preferably between 50:1 and 1:1, especially preferably between 10:1 and 1.5 to 1 and most especially preferably between 5:1 and 1.8:1. In particular these are stable, shear-diluting cleaning agents in the form of a gel containing a polysaccharide, a surfactant system and perfume components, which are wherein they contain a polysaccharide, preferably a xanthan gum, in amounts between 1 and 5 wt %, preferably 1 to 5 wt %, especially preferably 1.5 to 3.5 wt % and most especially preferably 1.8 to 3 wt % they contain as a component of the surfactant system a $C_{8-22}$ alkyl polyglycoside in amounts between 3 and 25 wt %, preferably 4 and 20 wt %, especially preferably 5 and 15 wt % and most especially preferably 5 and 12 wt % and they contain the perfume component(s) up to 15 wt %, preferably 2 to 12 wt %, especially preferably 3 to 8 wt %, and they optionally contain other ingredients such as lime-dissolving agents, dyes, microbicidal agents (e.g., isothiazoline mixtures, sodium benzoate or salicylic acid), pearlescent agents, stabilizers, cleaning enhancers and odor absorbers, and the agents have a viscosity of 30,000 to 150,000 mPas, measured with a Brookfield rotary viscometer, model RVT with a Helipath device and TA spindle at 1 rpm and 23° C.

If necessary, water-soluble and water-insoluble builders may also be present in the inventive gels. Water-soluble builders are then preferred because they usually have less tendency to form insoluble residues on hard surfaces. The usual builders which may be present within the scope of the invention include the low-molecular polycarboxylic acids and their salts, the homopolymeric and copolymeric polycarboxylic acids and their salts, citric acid and its salts, carbonates, phosphates and silicates. The water-insoluble builders include the zeolite, which may also be used as well as the mixtures of the aforementioned builder substances. The group of citrates is especially preferred. Other typical cleaning agents which may contain the inventive pro-fragrances include liquid or gel cleaners for hard surfaces, in particular, all-purpose cleaners, glass cleaners, floor and bathroom cleaners as well as special embodiments of such cleaners, which include acidic or alkaline forms of all-purpose cleaners as well as glass cleaners with an anti-rain effect. These liquid cleaning agents may also be present in one or more phases. In an especially preferred embodiment, the cleaners have two different phases.

"Cleaner" in the broadest sense is a term for formulations (usually containing a surfactant) with a very wide area of application and a very different composition, depending on the application. The most important market segments are household cleaners, industrial (technical) cleaners and institutional cleaners. Depending on the pH, a distinction is made between alkaline, neutral and acidic cleaners; according to the form in which it is offered, a distinction is made between liquid and solid cleaners (also in tablet form). These cleaners for hard surfaces should yield an optimal profile of use (in contrast with dishwashing agents, which are also classified in the product group of cleaners) both in a concentrated state and in dilute aqueous solution when combined with mechanical energy. Low-temperature cleaners manifest their effect without elevated temperature. Surfactants and/or alkali carriers, alternatively acids, optionally also solvents such as glycol ethers and lower alcohols are crucial for the cleaning effect. In general, the formulations also contain builders and, depending on the type of cleaner, bleaching agents, enzymes, microbicidal or disinfecting additives as well as perfume oils and dyes. Cleaners may also be formulated as microemulsions. The success of cleaning depends to a great extent on the type of dirt—which may also vary greatly geographically—and the properties of the surfaces to be cleaned.

Household cleaners may be formulated as universal cleaners or as special cleaners for ceramics, tiles, windows, plastics, (carpet) floors, cook-tops, baking ovens, microwave ovens, plumbing cleaners or bathroom or toilet cleaners. Pipe cleaners are adjusted to be alkaline and consist of, for example, solid sodium hydroxide and aluminum powder which, when dissolved, release hydrogen, which ensures a corresponding turbulence in the pipe segments to be cleared. In addition to containing surfactant and builder, sanitary cleaners mainly contain active ingredients to reduce the microbe count, whereby sodium hypochlorite, which was used previously, has been partially replaced by hydrogen peroxide or other peracid compounds. Toilet cleaners are mainly acidic but may sometimes also be adjusted to be alkaline, whereby in the former case, the phosphoric acid originally used and sodium bisulfate are largely replaced by organic acids, mainly citric acid. Special cleaners also include automotive cleaners, automobile windshield cleaners, wheel rim cleaners, engine cleaners and paint application equipment cleaners in the do-it-yourself area.

In addition to the components already mentioned, the inventive agents may also contain other additives and aids, such as those customary in such agents. These include, in particular, polymers, soil-release active ingredients, solvents (e.g., ethanol, isopropanol, glycol ether), solubilizers, hydrotropes (e.g., cumenesulfonate, octyl sulfate, butyl glucoside, butyl glycol), cleaning enhancers, viscosity regulators (e.g., synthetic polymers, such as polysaccharides, polyacrylates, naturally occurring polymers and their derivatives such as xanthan gum, other polysaccharides and/or gelatins), pH regulators (e.g., citric acid, alkanolamines or NaOH), disinfectants, antistatics, preservatives, bleach systems, enzymes, dyes and opacifiers or skin protectants.

The amount of such additives is usually no more than 12 wt % in the cleaning agent. The lower limit for use depends on the type of additive and may be up to 0.001 wt % or less in the case of dyes. The amount of auxiliaries is between 0.01 and 7 wt %, in particular, 0.1 and 4 wt %.

The aforementioned agents may also contain binders, which may be used alone or in mixture with other binders. Preferred binders include polyethylene glycols, 1,2-polypropylene glycols and modified polyethylene glycols and polypropylene glycols. The modified polyalkylene glycols include, in particular, the sulfates and/or disulfates of polyethylene glycols or polypropylene glycols with a relative molecular weight between 600 and 12,000 and, in particular, between 1,000 and 4,000. Another group consists of monosuccinates and/or disuccinates of polyalkylene glycols, which in turn have relative molecular weights between 600 and 6,000, preferably between 1,000 and 4,000.

Within the scope of this invention, polyethylene glycols include polymers for whose production $C_3$-$C_5$ glycols as well as glycerol and mixtures of these are used as initiator molecules in addition to ethylene glycol. Furthermore, ethoxylated derivatives such as trimethylolpropane with 5 to 30 ethylene oxides (EO) are also included. The polyethylene glycols that are preferred for use may have a linear or branched structure, but linear polyethylene glycols are preferred. in particular. The preferred polyethylene glycols include, in particular, those with relative molecular weights between 2,000 and 12,000, advantageously 4,000, whereby polyethylene glycols with relative molecular weights of less than 3,500 and greater than 5,000 may be used, in particular, in combination with polyethylene glycols with a relative molecular weight of 4,000, and such combinations advantageously have more than 50 wt %, based on the total amount of polyethylene glycols, polyethylene glycols with a relative molecular weight between 3,500 and 5,000. However, polyethylene glycols which are in a liquid state at room temperature and a pressure of 1 bar may also be used as binders; this refers mainly to polyethylene glycol with a relative molecular weight of 200, 400 and 600. However, these essentially liquid polyethylene glycols should be used only in a mixture with at least one other binder, whereby this mixture must again meet the inventive requirements, i.e., must have a melting point and/or a softening point at least higher than 45° C.

Low-molecular polyvinylpyrrolidones and derivatives of these with relative molecular weights up to max. 30,000 are also suitable as binders. Relative molecular weight ranges between 3,000 and 30,000 are preferred here, e.g., 10,000. Polyvinylpyrrolidones are preferably not used as exclusive binders but instead are used in combination with others, in particular, in combination with polyethylene glycols.

Other suitable binders have proven to be raw materials, said raw materials having detergent-active or cleaning-active properties, i.e., for example, nonionic surfactants with a melting point of at least 45° C. or mixtures of nonionic surfactants and other binders. The preferred nonionic surfactants include alkoxylated fatty alcohols or oxo alcohols, in particular, $C_{12-18}$ alcohols. Degrees of alkoxylation, in particular, degrees of ethoxylation, of 18 to 80 AO on the average, in particular, ethylene oxide (EO) per mol alcohol and mixtures of these have proven to be especially suitable. Especially fatty alcohols with an average of 18 to 35 EO, in particular, with an average of 20 to 25 EO have advantageous binder properties in the sense of the present invention. If necessary, ethoxylated alcohols with an average of a few EO units per mol alcohol may also be present in binder mixtures, e.g., tallow fatty alcohol with 14 EO. However, it is preferable to use these relatively low ethoxylated alcohols only in mixture with higher ethoxylated alcohols. The content of these relatively low ethoxylated alcohols in the binder, advantageously, amounts to less than 50 wt %, in particular, less than 40 wt %, based on the total amount of binder used. Nonionic surfactants that are generally used, especially in detergents or cleaning agents, such as $C_{12-18}$ alcohols with an average of 3 to 7 EO, which are liquid at room temperature, are preferably present in the binder mixtures only in amounts such that less than 2 wt % of these nonionic surfactants, based on the end product of the process, is made available. As already described above, however, it is less preferable to use nonionic surfactants that are liquid at room temperature in the binders. In an especially advantageous embodiment, such nonionic surfactants are, however, not a component of the binder mixture because they not only lower the softening point of the mixture but they may also contribute toward tackiness of the end product, and furthermore, due to their tendency to gel on coming in contact with water, they lead to gelation and do not meet the requirement of rapid dissolution of the binder/the partition in the end product to the desired extent. It is likewise preferable for conventional anionic surfactants that are used in detergents or cleaning agents or their precursors, the anionic surfactant acids, to be present in the binder mixture. Other nonionic surfactants that are suitable as binders include the fatty acid methyl ester ethoxylates, which do not tend to gel, in particular those with an average of 10 to 25 EO (for a more detailed description of this substance group, see below). Especially preferred representatives of this substance group include primarily the methyl esters based on $C_{16-18}$ fatty acids, e.g., hardened bovine tallow methyl esters with an average of 12 EO or with an average of 20 EO. In a preferred embodiment of the invention, a mixture containing $C_{12-18}$ fatty alcohol, based on coconut or tallow with an average of 20 EO, and polyethylene glycol with a relative molecular weight of 400 to 4,000 is used as the binder. In another preferred embodiment of the invention, a mixture containing mainly methyl esters based primarily on $C_{16-18}$ fatty acids and with an average of 10 to 25 EO, in particular, hardened bovine tallow methyl esters with an average of 12 EO or an average of 20 EO, and a $C_{12-18}$ fatty alcohol based on coconut or tallow with an average of 20 EO and/or polyethylene glycol with a relative molecular weight of 400 to 4,000, is used as the binder.

Binders based either only on polyethylene glycols with a relative molecular weight of 4,000 or on a mixture of $C_{12-18}$ fatty alcohol based on coconut or tallow with an average of 20 EO and one of the fatty acid methyl ester ethoxylates described above or on a mixture of $C_{12-18}$ fatty alcohol based on coconut or tallow with an average of 20 EO, one of the fatty acid methyl ester ethoxylates described above and a polyethylene glycol, in particular, with a relative molecular weight of 4,000, have proven to be especially advantageous embodiments of the invention.

The inventive agents may contain, e.g., carbonate/citric acid systems as suitable and well-known disintegration aids, but other organic acids may also be used. Swelling disintegration aids include, for example, synthetic polymers such as polyvinylpyrrolidone (PVP) or natural polymers and/or modified natural substances such as cellulose and starch and their derivatives, alginate or casein derivatives.

Within the scope of the present invention, disintegrants based on cellulose are used as the preferred disintegrants, so that preferably molded bodies of detergent and cleaning agent will contain such a disintegrant based on cellulose in amounts of 0.5 to 10 wt %, preferably 3 to 7 wt % and in particular 4 to 6 wt %. Pure cellulose has the formal empirical composition $(C_6H_{10}O_5)_n$ and, considered formally, is a β-1,4-polyacetal of cellobiose, which in turn is made up of two molecules of glucose. Suitable celluloses consist of approx. 500 to 5,000 glucose units and consequently have average molecular weight of 50,000 to 500,000. Within the scope of the present invention, cellulose derivatives, which are also available from cellulose by polymer-like reactions, may be used as disintegrants based on cellulose. Such chemically modified celluloses comprise, for example, products of esterifications and/or etherifications in which hydroxyhydrogen atoms have been substituted. However, celluloses in which the hydroxyl groups have been replaced by functional groups that are not bound by an oxygen atom may also be used as cellulose derivatives. The group of cellulose derivatives includes, for example, alkali celluloses, carboxymethylcellulose (CMC), cellulose esters and ethers as well as aminocelluloses. The aforementioned cellulose derivatives are preferably not used alone as disintegrants based on cellulose but instead are used in mixture with cellulose. The cellulose derivative content of these mixtures is preferably less than 50 wt %, especially preferably less than 20 wt %, based on the disintegrant based on cellulose. Pure cellulose free of cellulose derivatives is especially preferably used as the disintegrant based on cellulose.

The cellulose that is used as the disintegration aid is preferably not used in finely divided form but instead is converted to a coarser form, e.g., granular or compacted, before being added to the premixes to be pressed.

The particle size of such disintegrants is usually greater than 200 μm, preferably at least 90 wt % being between 300 and 1,600 μm, and in particular at least 90 wt % being between 400 and 1,200 μm.

Microcrystalline cellulose may be used as another disintegrant based on cellulose or as an ingredient of these components. This microcrystalline cellulose is obtained by partial hydrolysis of celluloses under such conditions that attack only the amorphous regions (approx. 30% of the total cellulose mass) of the celluloses and completely dissolve them, but leave the crystalline regions (approx. 70%) undamaged. Subsequent deaggregation of the microfine celluloses obtained by hydrolysis yields microcrystalline celluloses, which have primary particle sizes of approx. 5 μm and can be compacted to granules with an average particle size of 200 μm, for example.

In a preferred variant, the detergents and cleaning agents, in particular, in the form of molded bodies such as tablets, contain 0.5 to 10 wt %, preferably 3 to 7 wt % and, in particular, 4 to 6 wt % of one or more disintegration aids, each based on the weight of the molded body.

Another subject matter of the present invention is cosmetics (cosmetic agents) for treatment of hair or skin, containing the inventive pro-fragrances. These cosmetic (cosmetic agents) preferably contain the inventive pro-fragrances in amounts of 0.001 to 10 wt %, preferably from 0.01 to 5 wt %, especially preferably 0.02 to 3 wt % and, in particular, in amounts of 0.05 to 2 wt %, each based on the total composition of the cosmetic agent.

The total amount of scent substances in the cosmetic agents, however, is preferably between 0.01 and 5 wt %, especially preferably between 0.1 and 3 wt % and most especially preferably between 0.5 and 2 wt %, based on the total amount of the agent. Mixtures of various scent substances (from the various classes of scent substances mentioned above) which jointly produce an appealing scent note are preferably used. In this case, the total amount of the at least one scent substance is the amount of all scent substances in the mixture together, based on the total amount of the agent.

In a preferred embodiment, the cosmetic agents are aqueous preparations that contain surfactant active ingredients and are suitable, in particular, for treatment of keratin fibers, in particular human hair, or for treatment of skin.

The hair treatment agents mentioned above include, in particular, agents for treatment of human head hair. The most conventional agents of this category can be divided into shampoo detergents, hair care agents, hair setting and permanent hair waving agents as well as hair dyes and depilatories. The agents that are preferred according to this invention and contain surfactant active ingredients include in particular shampoos and treatment preparations. Such a hair washing agent or shampoo consists of 10 to 20 recipe ingredients, in individual cases up to 30 recipe ingredients. These aqueous preparations are usually in liquid form to pasty form.

The inventive cosmetics (cosmetic agents) usually contain other ingredients that are conventional for these agents.

The inventive cosmetic agents preferably contain surfactant active ingredients or detergent-active ingredients as additional ingredients. Fatty alcohol polyglycol ether sulfates (ether sulfates, alkyl ether sulfates) are preferably used here, partially in combination with other surfactants, usually anionics. In addition to the alkyl ether sulfates, preferred agents may additionally contain other surfactants such as alkyl sulfates, alkyl ether carboxylates, preferably with degrees of ethoxylation of 4 to 10, as well as surfactant protein-fatty acid condensates. Protein-abitic acid condensate should be mentioned here, in particular. Sulfosuccinic acid esters, amidopropyl-betaines, amphoacetates and amphodiacetates as well as alkyl polyglycosides are surfactants that are preferably used in shampoos.

Another group of ingredients is summarized by the term auxiliary substances and is extremely varied: for example, nonionic surfactant additives such as ethoxylated sorbitan esters or protein hydrolysates increase the compatibility and/or have an irritation-reducing effect, e.g., in baby shampoo; e.g., natural oils or synthetic fatty acid esters serve as moisturizing agents to prevent excessive removal of oil in shampooing; humectants include glycerol, sorbitol, propylene glycol (see propanediols), polyethylene glycols and other polyols. To improve wet combability and to reduce electrostatic charge buildup on the hair after drying, cationic surfactants, e.g., quaternary ammonium compounds, may be added to the shampoo. For a brilliant color appearance, dyes and/or pearlescent pigments may be added. To adjust the desired viscosity, thickeners of various substance classes may be used, and pH stability is achieved by buffers based on citrate, lactate or phosphate, for example. To ensure adequate stability and storage life, preservatives such as 4-hydroxybenzoic acid ester are added; oxidation-sensitive ingredients can be protected by adding antioxidants such as ascorbic acid, butylmethoxyphenol or tocopherol.

Another preferred group of ingredients include special active ingredients for special shampoos, e.g., oils, herbal extracts, proteins, vitamins and lecithins in shampoos for hair that becomes oily rapidly, for especially dry hair, stressed or damaged hair. Active ingredients in shampoos for controlling dandruff usually have a broad growth-inhibiting effect against fungi and bacteria. The fungistatic properties of pyrithione salts, in particular, have been shown to be the cause of the good antidandruff effect. To achieve a pleasant scent note, the shampoos contain perfume oils. The shampoos may contain the inventive silicic acid esters exclusively but it is also preferable if the shampoos contain not only these scent substances but others as well. All conventional scent substances allowed for use in shampoo may also be used here.

Hair care agents have the goal of preserving the natural condition of freshly washed hair as long as possible and restoring it if there is damage. Features characterizing this natural condition include a silky sheen, low porosity, a resilient and yet soft fullness and a pleasant smooth feel. An important prerequisite for this is a clean scalp, free of dandruff and without excessive oiliness. The hair care agents today include a variety of different products, the most important representatives of which are known as pretreatment agents, hair water, styling aids, hair rinses and hair repair kits and whose composition, like that of the shampoos, is broken down roughly into basic substances, auxiliary substances and special active ingredients.

The basic substances include fatty alcohols, especially cetyl alcohol (1-hexadecanol) and stearyl alcohol (1-octadecanol), waxes such as beeswax, wool wax (lanolin), sperm oil and synthetic waxes, paraffins, petrolatum, paraffin oil and as solvents mainly ethanol, 2-propanol and water. Additives include emulsifiers, thickeners, preservatives, antioxidants, coloring agents and perfume oils. The most important group of special active ingredients in hair care agents today are the quaternary ammonium compounds. A distinction is made between monomeric (e.g., alkyltrimethylammonium halide with mainly the lauryl, cetyl or stearyl group as the alkyl radical) and polymeric quaternary ammonium compounds (e.g., quaternary cellulose ether derivatives or poly(N,N-dimethyl-3,4-methylenepyrrolidinium chloride)). Their effect in hair care agents is based on the fact that the positive charge of the nitrogen atoms of this compound can be added to the negative charges of the keratin of hair; damaged hair contains more negatively charged acid groups because of its higher cysteic acid content and may therefore take up more quaternary ammonium compounds. Because of their cationic character, these compounds are also referred to as "cationic treatment substances" which have a smoothing effect on hair, improve combability, reduce electrostatic charge buildup, and improve the feel and sheen. The polymeric quaternary ammonium compounds adhere to hair so well that their effect can be detected even after several washings. Organic acids such as citric acid, tartaric acid or lactic acid are often used to adjust an acid medium. The water-soluble protein hydrolysates are absorbed well by the keratin of hair because of their close chemical relationship.

The largest group of special active ingredients in hair care agents comprise various plant extracts and plant oils.

These extracts are usually produced by extraction of the entire plant. However, in individual cases it may also be preferable to prepare the extracts exclusively from the flowers and/or leaves of the plant.

With regard to the plant extracts that are preferred according to the invention, reference is made in particular to the extracts listed in the table beginning on page 44 of the third edition of *Leitfaden zur Inhaltsstoffdeklaration kosmetischer Mittel* [Guideline for Declaration of Ingredients of Cosmetic Agents], published by the Industrial Association of Body Care and Detergents (IKW), Frankfurt.

According to this invention, the preferred extracts include especially those from green tea, oak bark, stinging nettle, witch hazel, hops, henna, chamomile, burdock root, horsetail, hawthorn, linden blossoms, almond, aloe vera, spruce needle, horse chestnut, sandalwood, juniper berry, coconut, mango, apricot, lemon, wheat, kiwi, melon, orange, grapefruit, sage, rosemary, birch, mallow, lady's smock, wild thyme, yarrow, thyme, lemon balm, restharrow, coltsfoot, marshmallow, meristem, ginseng and ginger root.

Extracts of green tea, oak bark, stinging nettle, witch hazel, hops, chamomile, burdock root, horsetail, linden blossom, almond, aloe vera, coconut, mango, apricot, lemon, wheat, kiwi, melon, orange, grapefruit, sage, rosemary, birch, lady's smock, wild thyme, yarrow, restharrow, ginseng and ginger root are especially preferred. Most especially preferred are the extracts of green tea, almond, aloe vera, coconut, mango, apricot, lemon, wheat, kiwi and melon.

As extraction agents for producing the aforementioned plant extracts, water, alcohols and mixtures thereof may be used. Of the alcohols, low alcohols such as ethanol and isopropanol are preferred, but in particular, polyvalent alcohols such as ethylene glycol and propylene glycol are preferred as the sole extraction agent as well as in mixture with water. Plant extracts based on water/propylene glycol in a ratio of 1:10 to 10:1 have proven to be especially suitable.

The plant extracts may be used in both pure and diluted form according to this invention. If they are used in diluted form, they usually contain approx. 2 to 80 wt % active substance and as a solvent the extraction agent or extraction agent mixture used in extracting them.

In addition, it may be preferable to use mixtures of several plant extracts, in particular, to different plant extracts in the inventive agents.

To avoid moisturizing too rapidly, some hair waters contain substances such as certain tar ingredients, cysteic acid derivatives or glycyrrhizin; the intended reduction in sebaceous gland production has also not been proven conclusively. However, the efficacy of antidandruff agents has been satisfactorily proven. They are therefore used in the corresponding hair waters and similar hair care agents.

The aqueous preparations for treatment of skin include, in particular, preparations for care of human skin. This treatment begins with cleaning for the soaps which are used primarily. A distinction is made here between solid soap, usually in pieces, and liquid soap. Accordingly, the cosmetic agents in a preferred embodiment are in the form of molded bodies containing surfactant ingredients. In a preferred embodiment, the most important ingredients of such molded bodies are the alkali salts of the fatty acids of natural oils and fats, preferably with chains of 12-18 carbon atoms. Since lauric acid soaps form suds especially well, the lauric acid-rich coconut and palm kernel oils are preferred raw materials for production of fine soaps. The sodium salts of fatty acid mixture are solid, whereas the potassium salts are soft and pasty. For saponification, the dilute sodium hydroxide or potassium hydroxide solution is added to the fat raw materials in a stoichiometric ratio, so that the finished soap contains a lye excess of max. 0.05%. In many cases, soaps today are no longer prepared directly from fats but instead are prepared from the fatty acids obtained by splitting off fat. The usual soap additives include fatty acids, fatty alcohols, lanolin, lecithin, vegetable oils, partial glycerides and similar fat-like substances for moisturizing cleaned skin, antioxidants such as ascorbyl palmitate or tocopherol to prevent autoxidation of soap (rancidity), complexing agents such as nitrilotriacetate to bind traces of heavy metals which could act as catalysts in autoxidative spoilage, perfume oils to achieve the desired scent notes, coloring agents to color the pieces of soap and special additives, if necessary.

Liquid soaps are based on potassium salts of natural fatty acids as well as on synthetic anionic surfactants. They contain fewer detergent-active substances in aqueous solution than do solid soaps and have the usual additives, if necessary with viscosity-regulating components such as pearlescent additives. Because of their convenient and hygienic use from dispensers, they are preferably used in public restrooms and the like. Washing lotions for especially sensitive skin are based on mild synthetic surfactants with additives of skin care substances, adjusted to a neutral pH or weakly acidic (pH 5.5).

There are a number of other preparations for cleaning and care of mainly the skin of the face such as face lotion, cleaning lotions, milks, creams, pastes; face packs are used for cleaning but primarily for refreshing and care of facial skin. Face lotions are usually aqueous alcoholic solutions with small amounts of surfactant and other skin care substances. Cleaning lotions, milk, creams and pastes are usually based on O/W emulsions with a relatively low amount of fat components with cleaning and care additives. Scruffing and peeling preparations contain mild keratolytic substances for removing the top horny layers of dead skin, in part with abrasive powder as additives.

Agents for cleaning treatment of uncleaned skin also contain antibacterial and anti-inflammatory substances because the accumulations of sebum in comedones (pimples) constitute a culture medium for bacterial infections and tend to lead to inflammation. The broad range of different skin cleaning products that are available varies in composition and content of various active ingredients, coordinated with the various types of skin and for special treatment goals.

The bath additives offered for cleaning skin in the bathtub or shower have been widely used. Bath salts and bath tablets should soften, color and perfume the bath water and usually do not contain any detergent-active substances. By softening the bath water, they promote the cleaning power of soaps but should primarily have a refreshing effect and enhance the bath experience. Bubble baths have a greater importance. With a larger amount of moisturizing and skin care substances, we also speak of cream baths.

The inventive cosmetics (cosmetic agents) may be present in different preparation forms.

The most important are skin creams, skin lotions, skin oils and skin gels. The creams and lotions are based on emulsions in O/W (oil-in-water) form or W/O (water-in-oil) form. The main ingredients of the oil and/or fat or lipid phase include fatty alcohols, fatty acids, fatty acid esters, waxes, petrolatum, paraffins and other fat and oil components mainly of a natural origin. In addition to water, the aqueous phase contains moisture-regulating and moisture-preserving substances as the main skin care active ingredients plus agents to regulate consistency and/or viscosity. Additional additives such as preservatives, antioxidants, complexing agents, perfume oils, coloring agents as well as special active ingredients are added to one of the aforementioned phases, depending on their solubility and stability properties. The choice of the emulsifier system is essential for the emulsion type and its properties. It can be selected according to the HLB system.

In addition, the skin care agents may contain other special active ingredients, e.g., milk protein products, egg yolk, lecithins, lipoids, phosphatides, cereal seed oils, vitamins, especially vitamin F and biotin, which was previously referred to as the skin vitamin (vitamin H) as well as hormone-free placenta extracts.

Skin oils are some of the oldest forms of skin care products and are still in use today. They are based on nondrying vegetable oils such as almond oil or olive oil with additives of natural vitamin oils such as wheat germ oil or avocado oil and oil-based plant extracts from St. John's wort, chamomile, etc.

Skin gels are semisolid transparent products that are stabilized through appropriate gelatinizing agents. A distinction is made between oleogels (anhydrous), hydrogels (oil free) and oil/water gels. The choice of type will depend on the desired intended application. The oil/water gels have high emulsifier contents and have certain advantages in comparison with emulsions from the standpoint of both aesthetics and applications.

Other cosmetic agents that are preferred according to the invention include agents for influencing body odor. Deodorizing agents are intended here, in particular. Such deodorants may mask, remove or destroy odors. Unpleasant body odors are formed from bacterial decomposition of perspiration, in particular, in the moist, warm axillary cavities, where microorganisms find good conditions for survival. Accordingly, the most important ingredients of deodorants are microbistatic substances. In particular, such microbistatic substances that have a largely selective efficacy with respect to the bacteria responsible for body odor are preferred. Preferred active ingredients, however, have only a bacteriostatic effect and by no means completely kill off the bacterial flora. The microbistatic agents may in general include all suitable preservatives with a specific action against gram-positive bacteria. For example, these include Irgasan DP 300 (trichlosan, 2,4,4'-trichloro-2'-hydroxydiphenyl ether), chlorhexidine (1,1'-hexamethylenebis(5-(4'-chlorophenyl)biguanide) as well as 3,4,4'-trichlorocarbanilide. Quaternary ammonium compounds are also suitable in principle. Because of their high antimicrobial efficacy, all these substances are preferably used only in low concentrations of approx. 0.1 to 0.3 wt %. In addition, numerous perfumes also have antimicrobial properties. Accordingly, such perfumes having antimicrobial properties are preferably used in deodorants. Farnesol and phenoxyethanol may be mentioned here, in particular. It is therefore preferable, in particular, if the inventive deodorants contain such perfumes which have their own bacteriostatic effect. These perfumes may preferably again be present in the form of silicic acid esters. However, it is also possible for these perfumes, which have an antibacterial efficacy, not to be used in the form of silicic acid esters and then to be used in mixtures with other perfumes which are in the form of silicic acid esters. Another group of important ingredients of deodorants is the enzyme inhibitors, which inhibit the decomposition of perspiration through enzymes such as citric acid triethyl ester or zinc glycinate. Essential ingredients of deodorants also include the antioxidants, which should prevent oxidation of the components of perspiration.

Another subject matter of the present invention is the use of the inventive pro-fragrances for prolonging the scent effect of scent substances.

Owing to the excellent suitability of the inventive compounds for use in detergents and cleaning agents, use of the inventive pro-fragrances in liquid or solid detergents and cleaning agents, in particular, preferably as a scent substance, is another subject matter of the present invention.

The inventive pro-fragrances are likewise excellently suited for use in cosmetics (cosmetic agents) so another subject matter of the present invention is the use of the inventive pro-fragrances in cosmetics (cosmetic agents) for the treatment of skin and hair, in particular, preferably as a scent substance.

A subject matter of the present invention is likewise the use of the inventive pro-fragrances together with other conventional scent substances which are incorporated preferably by traditional methods into agents such as detergents and cleaning agents as well as fabric softeners and cosmetics.

Another subject matter of the present invention is the method for prolonging the scent perception of detergents or cleaning agents, fabric softeners or cosmetics or solid surfaces treated with them, wherein the inventive pro-fragrances or mixtures thereof are added to the detergents or cleaning agents, fabric softeners or cosmetics.

The inventive pro-fragrances then preferably gradually release the derivatized scent substances contained therein by hydrolysis.

The inventive compounds and agents under ambient conditions have a good hydrolytic cleavability. They also have good stability in storage in an alkaline environment, such as that encountered in detergents and dishwashing agents, for example.

The invention also relates to a method for prolonging the scent perception of detergents or cleaning agents, fabric softeners or cosmetics or solid surfaces treated with these agents, in which inventive compounds or mixtures thereof are incorporated into the detergents or cleaning agents, fabric softeners or cosmetics. The scent substances are then preferably released again by hydrolysis.

The invention will now be illustrated in greater detail by the following examples.

Synthesis of 1-aza-3,7-dioxabicyclo[3.3.0]octanes.

AA1: General operating procedure for synthesis of 1-aza-3, 7-dioxabicyclo[3.3.0]octanes, amino alcohol/aldehyde ratio 1:2.

The amino alcohol is placed in toluene in a 1:2 ratio with the aldehyde under a nitrogen atmosphere. The reaction mixture is heated to T=120° C., whereupon the amino alcohol slowly goes into solution. Reflux on the water separator for 7 hours. Rotating and drying of the clear, faintly yellowish solution in a high vacuum.

AA2: General operating procedure for synthesis of 1-aza-3, 7-dioxabicyclo[3.3.0]octanes, amino alcohol/aldehyde ratio 1:2 in situ.

The amino alcohol is placed first with the aldehyde in a 1:2 ratio under a nitrogen atmosphere. The reaction mixture is heated to T=100° C.-140° C., whereupon the reactants go into solution slowly or melt. The reaction mixture is heated until no more reaction water can be distilled off. The clear slightly yellowish solution is dried in a high vacuum.

EXAMPLE 1

Synthesis of 1-aza-3,7-dioxa-2,8-dioctyl-5-alkylbi-cyclo-[3.3.0]octane a) with $R^6$=H according to AA1: 1-aza-3,7-dioxa-2,8-dioctylbicyclo[3.3.0]octane 2-Amino-1,3-propanediol m=1.37 g, M=91.1 g/mol (15 mmol), Octanal m=3.85 g, M=128.21 g/mol (30 mmol)

Yield=85%, m=3.95 g yellowish clear liquid, purity GC 90% with $R^6$=H according to AA2: 1-aza-3,7-dioxa-2,8-dioctylbi-cyclo-[3.3.0]octane 2-Amino-1,3-propanediol m=1.37 g, M=91.1 g/mol (15 mmol), Octanal m=3.85 g, M=128.21 g/mol (30 mmol)

Yield=88%, m=4.12 g yellowish clear liquid, purity GC 92%

$^1$H NMR (CDCl$_3$) characteristic signals of the bicyclic compound: δ 4.30 (dd, 2H), 4.08 (m, 2H), 3.80 (m, 1H), 3.62 (m, 2H)

b) with $R^6$=Me according to AA1: 1-aza-3,7-dioxa-5-methyl-bicyclo[3.3.0]octane 2-Amino-2-methyl-1,3-propanediol m=1.89 g, M=105.13 g/mol (18 mmol).

Octanal m=4.61 g, M=128.21 g/mol (36 mmol)

Yield=98%, m=5.73 g yellowish clear liquid, purity GC 94%

$^1$H NMR (CDCl$_3$) characteristic signals of the bicyclic compound: δ 4.34 (dd, 2H), 3.71 (d, 2H), 3.63 (d, 2H).

c) with $R^6$=hydroxymethyl according to AA1: 1-aza-3,7-di-oxa-2,8-dioctyl-5-hydroxymethylbicyclo[3.3.0]octane.

2-Amino-2-hydroxymethyl-1,3-propanediol m=1.82 g, M=121.13 g/mol (15 mmol)

Octanal m=3.85 g, M=128.21 g/mol (36 mmol)

Yield=94%, m=4.81 g clear highly viscous liquid, purity GC 95.8%

$^1$H NMR (CDCl$_3$) characteristic signals of the bicyclic compound: δ 4.41 (dd, 2H), 3.88 (d, 2H), 3.61 (d, 2H).

d) with $R^6$=ethyl according to AA1: 1-aza-3,7-dioxa-2,8-dioctyl-5-ethylbicyclo[3.3.0]octane 2-Amino-2-ethyl-1,3-propanediol m=3.57 g, M=119.16 g/mol (30 mmol).

Octanal m=7.70 g, M=128.21 g/mol (60 mmol)

Yield=96%, m=9.74 g clear highly viscous liquid, purity GC 94.7%

$^1$H NMR (CDCl$_3$) characteristic signals of the bicyclic compound: δ 4.34 (dd, 2H), 3.80 (d, 2H), 3.57 (d, 2H).

EXAMPLE 2

Synthesis of 1-aza-3,7-dioxa-2,8-di(2,6-dimethyl-5-heptenyl)-5-alkyl-bicyclo[3.3.0]octane a) with $R^6$=H according to AA1: 1-aza-3,7-dioxa-2,8-di(2, 6-dimethyl-5-heptenyl)-bicyclo[3.3.0]octane 2-Amino-1,3-propanediol m=1.37 g, M=91.1 g/mol (15 mmol), 2,6-Dimethylheptyl-5-enal m=5.34 g, M=178.12 g/mol (30 mmol)

Yield=94%, m=7.1 g yellowish clear liquid, purity GC 86%

$^1$H NMR (CDCl$_3$) characteristic signals of the bicyclic compound: δ 4.24 (dd, 2H), 4.04 (m, 2H), 3.68 (m, 1H), 3.58 (m, 2H)

b) with $R^6$=Me according to AA1: 1-aza-3,7-dioxa-2,8-di(2, 6-dimethyl-5-heptenyl)-5-methyl-bicyclo[3.3.0]octane 2-Amino-2-methyl-1,3-propanediol m=1.78 g, M=105.13 g/mol (17 mmol)

2,6-Dimethylheptyl-5-enal m=6.05 g, M=178.12 g/mol (34 mmol)

Yield=85%, m=5.41 g yellowish clear liquid, purity GC 87%

$^1$H NMR (CDCl$_3$) characteristic signals of the bicyclic compound: δ 4.12 (m, 2H), 3.64 (m, 2H), 3.46 (m, 2H).

c) with $R^6$=hydroxymethyl according to AA1: 1-aza-3,7-dioxa-2,8-di(2,6-dimethyl-5-heptenyl)-5-hydroxymethylbicyclo[3.3.0]octane
2-Amino-2-hydroxymethyl-1,3-propanediol m=1.82 g, M=121.13 g/mol (15 mmol)
2,6-Dimethylheptyl-5-enal m=5.34 g, M=178.12 g/mol (30 mmol)
Yield=97%, m=5.35 g clear highly viscous liquid, purity GC 99.1%
$^1$H NMR (CDCl$_3$) characteristic signals of the bicyclic compound: δ 4.29 (dd, 2H), 4.18 (m, 2H).

d) with $R^6$=ethyl according to AA1: 1-aza-3,7-dioxa-2,8-di(2,6-dimethyl-5-heptenyl)-5-ethyl-bicyclo[3.3.0]octane
2-Amino-2-ethyl-1,3-propanediol m=5.21 g, M=119.16 g/mol (43.7 mmol)
2,6-Dimethylheptyl-5-enal m=12.3 g, M=128.21 g/mol (87.4 mmol)
Yield=79%, m=12.51 g clear highly viscous liquid, purity GC 92.9%
$^1$H NMR (CDCl$_3$) characteristic signals of the bicyclic compound: δ 4.16 (m, 2H), 3.69 (m, 2H), 3.51 (m, 2H).

EXAMPLE 3

Synthesis of 1-aza-3,7-dioxa-2,8-di(3-(4-tert-butyl phenyl)butyl)-5-alkyl-bicyclo[3.3.0]octane a) with $R^6$=H according to AAV1: 1-aza-3,7-dioxa-2,8-di(3-(4-tertbutylphenyl)butyl)-bicyclo[3.3.0]octane
2-Amino-1,3-propanediol m=1.37 g, M=91.1 g/mol (15 mmol),
3-(4-tert-butylphenyl)butanal m=6.12 g, M=204.3/mol [sic; g/mol] (30 mmol)
Yield=100%, m=6.9 g yellowish clear liquid, purity GC 90%
$^1$H NMR (CDCl$_3$) characteristic signals of the bicyclic compound: δ 4.34 (dd, 2H), 4.12 (m, 2H), 3.82 (m, 1H), 3.66 (m, 2H)

b) with $R^6$=Me according to AA1: 1-aza-3,7-dioxa-2,8-di(3-(4-tertbutylphenyl)butyl)-5-methyl-bicyclo[3.3.0]octane
2-Amino-2-methyl-1,3-propanediol m=1.37 g, M=105.13 g/mol (13 mmol)
3-(4-tert-butylphenyl)butanal m=5.31 g, M=204.3/mol [sic; g/mol] (26 mmol)
Yield=97%, m=6.04 g yellowish clear liquid, purity GC 93%
$^1$H NMR (CDCl$_3$) characteristic signals of the bicyclic compound: δ 4.24 (33, 2H), 4.16 (m, 2H).

c) with $R^6$=hydroxymethyl according to AA1: 1-aza-3,7-dioxa-2,8-di(3-(4-tert-butylphenyl)-butyl)-5-hydroxymethylbicyclo[3.3.0]octane
2-Amino-2-hydroxymethyl-1,3-propanediol m=1.82 g, M=121.13 g/mol (15 mmol)
3-(4-tert-butylphenyl)butanal m=6.12 g, M=204.3/mol [sic; g/mol] (30 mmol)
Yield=97%, m=7.19 g clear highly viscous liquid, purity GC 93%
$^1$H NMR (CDCl$_3$) characteristic signals of the bicyclic compound: δ 4.28 (dd, 2H), 4.19 (m, 2H).

d) with $R^6$=ethyl according to AA1: 1-aza-3,7-dioxa-2,8-di(3-(4-tert-butylphenyl)butyl)-5-ethyl-bicyclo[3.3.0]octane
2-Amino-2-ethyl-1,3-propanediol m=1.78 g, M=119.16 g/mol (15 mmol)
3-(4-tert-butylphenyl)butanal m=6.12 g, M=204.3/mol [sic; g/mol] (30 mmol)
Yield=89%, m=6.60 g clear highly viscous liquid, purity GC 88%
$^1$H NMR (CDCl$_3$) characteristic signals of the bicyclic compound: 4.26 (m, 1H), 4.18 (dd, 1H), 3.85 (m, 2H), 3.63 (m, 2H).

EXAMPLE 4

Synthesis of 1-aza-3,7-dioxa-2-phenylacetyl-8-octyl-bicyclo[3.3.0]octane

First step according to AAV1:
2-Amino-1,3-propanediol m=1.37 g, M=91.1 g/mol (15 mmol)
1-Phenylethanon m=5.79 g, M=193.24 g/mol (30 mmol)
t=24 hours, rotation of the initially bluish solution and drying in a high vacuum, then the solution was slightly yellowish and clear.
Monosubstituted oxazolidine
Yield=55%, m=2.2 g clear yellowish liquid, purity GC 98.5%.
$^1$H NMR (CDCl$_3$): [illegible] 7.59 (dd, 2H), 7.34 (m, 3H), 4.11 (dd, 0.5H), 3.76 (m, 2.5H), 3.42 (dd, 0.5H), 3.30 (m, 1H), 3.06 (m, 0.5H), 1.69 (s, 1.5H), 1.66 (s, 1.5H).
Second step according to AAV1:
[2-Methyl-2-phenyl-1,3-oxazolidin-4-yl]methanol m=1.19 g, M=193.24 g/mol (5.7 mmol)
Octanal m=0.73 g, M=128.21 g/mol (5.7 mmolmmol [sic])
Yield=99.9%, m=1.83 g yellowish clear liquid, purity GC 80%
$^1$H NMR (CDCl$_3$) characteristic signals of the bicyclic compound: δ 4.90 (dd, 2H), 4.38 (dd, 1H), 4.10 (m, 2H), 4.05 (dd, 1H).

Smell Test.

For the smell test described below, 0.2 mmol of the perfume substance derivative in dichloromethane or ethanol was dissolved in 1 mL solvent. A perfume strip was immersed 2 cm deep into the solution and then allowed to dry.

The underivatized perfume substance was always used as the reference for the scent impression. The perfume substance was also dissolved in an amount of 0.2 mmol in 1 mL ethanol for this purpose. A perfume strip was immersed 2 cm deep into the solution and then allowed to dry.

The perfume strips were smelled once in the dry state and then smelled daily moist/sprayed. Water (pH=7) and the corresponding buffer solutions with pH 6-1 were used for spraying. The scent intensity was evaluated by three trained volunteers on a scale of 0 to 4, where 4 is the highest score and 0 stands for no perception of scent.

| Definition of the scale | |
|---|---|
| 4 | strong |
| 3 | intense |
| 2 | pleasant |
| 1 | perceptible |
| 0 | not perceptible |

| 1-aza-3,7-dioxa-2,8-dioctyl-5-alkylbicyclo[3.3.0]octane | Dry | pH = 7 H₂O | pH = 4 | pH = 2 | pH = 1 | Octanal with water | Octanal dry |
|---|---|---|---|---|---|---|---|
| Day 0 | 2 | 1-2 | 2 | 2 | 4 | 2 | 2 |
| Day 1 | 2 | 1-2 | 2 | 2 | 3 | 1 | 1 |
| Day 2 | 2 | 1-2 | 2 | 2 | 3 | 1 | 0-1 |
| Day 3 | 1 | 1-2 | 1-2 | 1-2 | 2-3 | 1 | 0-1 |
| Day 7 | 1 | 1-2 | 1-2 | 1-2 | 2 | 1 | 0 |

| Synthesis of 1-aza-3,7-dioxa-2,8-di(2,6-dimethyl-5-heptenyl)-5-alkyl-bicyclo[3.3.0]octane | Dry | pH = 7 H₂O | pH = 4 | pH = 2 | pH = 1 | 2,6-Dimethyl-heptyl-5-enal with water | 2,6-Dimethyl-heptyl-5-enal, dry |
|---|---|---|---|---|---|---|---|
| Day 0 | 1 | 2-3 | 2-3 | 2-3 | 2-3 | 2 | 1-2 |
| Day 1 | 1 | 2 | 2 | 2 | 2-3 | 0 | 0 |
| Day 2 | 0-1 | 2 | 2 | 2 | 2-3 | 0 | 0 |
| Day 3 | 0-1 | 1 | 1-2 | 2 | 2-3 | 0 | 0 |
| Day 7 | 0-1 | 1 | 1-2 | 2 | 2-3 | 0 | 0 |

| 1-aza-3,7-dioxa-2,8-di(3-(4-tert-butylphenyl)-butyl)-5-alkylbicyclo[3.3.0]-octane | Dry | pH = 7 H₂O | pH = 4 | pH = 2 | pH = 1 | 3-(4-tert-butylphenyl)-butanal with water | 3-(4-tert-butylphenyl)-butanal, dry |
|---|---|---|---|---|---|---|---|
| Day 0 | 3 | 3 | 3 | 3 | 3 | 2-3 | 2 |
| Day 1 | 2 | 2 | 2 | 2 | 2 | 2 | 1 |
| Day 2 | 1 | 1-2 | 1-2 | 1 | 2 | 1 | 0 |
| Day 3 | 1 | 1 | 1 | 1 | 1-2 | 0-1 | 0 |
| Day 7 | 0-1 | 1 | 1 | 1 | 1-2 | 0-1 | 0 |

The invention claimed is:

1. A 1-aza-3,7-dioxabicyclo[3.3.0]octane compound of general formula (I)

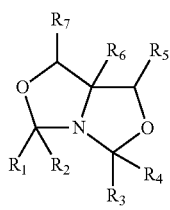

wherein each of $R^1$, $R^2$, $R^3$, $R^4$ independently yields a scent aldehyde or scent ketone in a compound of general formulae $R^1$—C(=O)—$R^2$ and $R^3$—C(=O)—$R^4$; with the proviso that one of $R^1$ and $R^2$, and one of $R^3$ and $R^4$ are not simultaneously hydrogen;

$R^6$ is H or an alkyl group which can be substituted by one or two hydroxyl groups and/or an amino group and/or wherein up to eight nonvicinal $CH_2$ groups can be replaced by —O—;

each of $R^5$ and $R^7$ is independently H or $C_1$-$C_6$ alkyl; and wherein the scent ketone is selected from the group consisting of buccoxime; iso asmone; methyl-β-naphthyl ketone, musk indanone; tonalide/musk plus; α-damascone, β-damascone, δ-damascone, isodamascone, damascenone, damarose, methyl dihydroiasmonate, menthone, carvone, camphor, fenchone, α-ionene, β-ionone, dihydro-β-ionone, γ-methyl, ionone, fleuramone, dihydroiasmone, cis-jasmone, iso-E-super, methyl cedrenyl ketone or methyl cedrylone, acetophenone, methyl acetophenone, paramethoxyacetophenone, methyl-β-naphthyl ketone, benzylacetone, benzophenone, parahydroxy-phenylbutanone, celery ketone or livescone, 6-isopropyl-decahydro-2-naphthone, dimethyloctenone, freskomenth, 4-(1-ethoxyyinyl)-3,3,5,5-tetramethylcyclohexanone, methylheptenone, 2-(2-(4-methyl-3-cyclohexen-1-yl)propyl) cyclopentanone, 1-(p-menthen-6(2)-yl)-1-propanone, 4-(4-hydroxy-3-methoxyphenyl)-2-butanone, 2-acetyl-3,3-dimethylnorbomane, 6,7-dihydro-1,1,2,3,3-pentamethyl-4(5H)indanone, 4-damascole, dulcinyl or cassion, gelsone, hexylone isocyclemon E, methyl cyclocitron, methyl lavendel ketone, orivone, para-tert-butylcyclohexanone, verdone, delphone, muscone, neobutenone, plicatone, veloutone, 2,4,4,7-tetramethyloct-6-en-3-one, tetramerane, hedione and mixtures thereof; and wherein the scent aldehyde is selected from the group consisting of melonal, triplal, ligustral, adoxal; anisaldehyde; cymal; ethyl vanillin; florhydral; helional; heliotropin; hydroxycitronellal; koavone; lauryl aldehyde, lyral, methyl nonylacetaldehyde; p,t-bucinal; phenyl acetaldehyde; undecylene aldehyde; vanillin; 2,6,10-trimethyl-9-undecenal, 3-dodecen-1-al, α-n-amylcinnamaldehyde, 4-methoxybenzaldhyde, benzaldehyde, 3-(4-tert-butylphenyl)propanal, 2-methyl-3-(para-methoxyphenylpropanal), 2-methyl-4-(2,6,6-trimethyl-2(1)-cyclohexen-1-yl)butanal, 3-phenyl-2-propenal, cis-/trans-3,7-dimethyl-2,6-octadien-1-al, 3,7-dimethyl-6-octen-l-al, [(3,7-dimethyl-6-octeny) oxy]acetaldehyde, 4-isopropylbenzaldehyde, 1,2,3,4,5, 6,7,8-octahydro-8,8-dimethyl-2-naphthaldehyde, 2,4-dimethyl-3-cyclo-hexen-1-carboxyaldehyde, 2-methyl-3(isopropylphenyl)propanal, decylaldehyde, 2,6-dimethyl-5-heptenal; 4-(tricycle[5.2.1.0(2,6)] decylidene-8)butanal; octahydro-4,7-methano-1H-indenecarboxaldehyde; 3-ethoxy-4-hydroxybenzaldehyde, para-ethyl -α, α-dimethylhydrocinnamaldehyde, α-methyl-3,4(methylenedioxy)hydrocinnamaldehyde, 3,4-methylenedioxybenzaldehyde, α-n-hexylcinnamaldehyde, m-cyumene-7-carboxaldehyde, α-methylphenylacetaldehyde, 7-hydroxy-3,7-dimethyloctanal, undecenal, 2,4,6-trimethyl-3-cyclohexene-1-carboxaldehyde, 4-(3)(4-methyl-3-pentenyl)-3cyclohexene carboxaldehyde, 1-dodecanal, 2,4-dimethylcyclohexene-3-carboxaldehyde, 4-(4-hydroxy-4-methylpentyl)-3-cyclohexene-1-carboxaldehyde, 7-methoxy-3,7-dimethyloctan-1-al, 2-methylundecanal, 2-methyldecanal, 1-nonanal, 1-octanal, 2,6,10-trimethyl-5,9-undecadienal, 2-methyl-3-(4-tert-1-butyl)propanal, dihydrocinnamaldehyde, 1-methyl-4-(4-methyl-3-pentenyl)-3-cyclohexene-1-carboxaldehyde, 5- or 6-methoxyhexahydro-4,7-methanoindan-1- or 2-carboxyaldehyde; 3,7-dimethyloctan-1-al, 1-undecanal, 10-undecen-1-al, 4-hydroxy-3-methoxybenzaldehyde, 1-methyl-3-(4-methyl pentyl)-3-cyclohexenecarboxyaldehyde, 7-hydroxy-3,7-dimethyloctanal; trans-4-decenal, 2,6-nonadienal, para-tolylacetaldehyde; 4-methylphenylacetaldehyde, 2-methyl-4-(2,6,6-trimethyl-1-cyclohexen-1-yl)-2-butenal, ortho-methoxycinnamaldehyde, 3,5,6-trimethyl-3-cyclohexenecarboxaldehyde; 3,7-dimethyl-2-methylene-6-octenal, phenoxyacetaldehyde; 5,9-dimethyl-4,8-decadienal, peony aldehyde (6,10-dimethyl-3-oxa-5,9-undecadien-1-al), hexahydro-4,7-methanoindane-1-carboxaldehyde, 2-methyloctanal, α-methyl-4-(1-methylethyl)-benzeneacetaldehyde, 6,6-dimethyl-2-norpinene-2-propionaldehyde, para-methylphenoxy-acetaldehyde; 2-methyl-3-phenyl-2-propen-1-al, 3,5,5-trimethylhexanal, hexahydro-8,8-dimethyl-2-naphthaldehyde, 3-propylbicyclo[2.2.1]-hept-5-ene-2-carbaldehyde, 9-decenal, 3-methyl-5-phenyl-1-pentanal, methyinonylacetaldehyde, 1-p-menthene-q-carboxaldehyde, lilial citral, 1-decanal, florhydral, 2,4-dimethyl-3-cyclohexene-1-carboxaldehyde; preferred aldehydes may be selected from cis/trans-3,7-dimethyl-2,6octadien-l-al; heliotropin; 2,4,6-trimethyl-3-cyclohexene-1-carboxaldehyde; 2,6-nonadienal; α-n-amyl-cinnamaldehyde, α-n-hexyl-cinnamaldehyde, p-tert-bucinal; lyral, cymal, methylnonylacetaldehyde, trans-2-nonenal, lilial, trans-2-nonenal and mixtures thereof.

2. The compound of claim 1 wherein in the structural element —$CR^1R^2$, the structural element —$CR^3R^4$, $R^1$, $R^2$, $R^3$, $R^4$ together are comprised of at least four carbon atoms.

3. The compound of claim 1 wherein each of $R^2$, $R^4$, $R^5$, $R^6$, and $R^7$ is hydrogen.

4. A composition comprising a compound of claim 1 and a compound of the formula

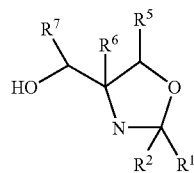

wherein $R^1$, $R^2$, $R^5$, $R^6$ and $R^7$ are the same as defined in claim 1.

5. A composition comprising a compound of claim 1 and a component selected from the group consisting of a detergent, a fabric softener and a cosmetic.

6. The composition of claim 5 wherein the amount of the compound is less than 5 wt %.

7. The composition of claim 5 wherein the composition is a solid, liquid or a gel.

8. The composition of claim 7 wherein the composition is a solid.

9. The composition of claim 8 wherein the solid is a powder, granule, or tablet.

10. The composition of claim 7 wherein the composition is a liquid.

11. The composition of claim 10 wherein the liquid is a solution, emulsion or dispersion.

12. The composition of claim 7 wherein the composition is a gel.

13. A composition comprising a compound of claim 1 and a deodorant.

14. A composition comprising a compound of claim 1 and a hair or skin treatment agent.

* * * * *